US008822492B2

(12) United States Patent
Schachter

(10) Patent No.: US 8,822,492 B2
(45) Date of Patent: *Sep. 2, 2014

(54) USE OF HUPERZINE FOR DISORDERS

(75) Inventor: Steven C. Schachter, Sharon, MA (US)

(73) Assignee: President and Fellows of Harvard College, Cambridge, MA (US)

(*) Notice: Subject to any disclaimer, the term of this patent is extended or adjusted under 35 U.S.C. 154(b) by 6 days.

This patent is subject to a terminal disclaimer.

(21) Appl. No.: 13/347,136

(22) Filed: Jan. 10, 2012

(65) Prior Publication Data

US 2012/0107392 A1 May 3, 2012

Related U.S. Application Data

(63) Continuation of application No. 12/779,612, filed on May 13, 2010, now Pat. No. 8,093,262, which is a continuation of application No. 11/439,557, filed on May 23, 2006, now Pat. No. 8,193,212.

(60) Provisional application No. 60/683,745, filed on May 23, 2005, provisional application No. 60/756,141, filed on Jan. 4, 2006.

(51) Int. Cl.
A61K 9/127 (2006.01)
A61P 25/08 (2006.01)
A61K 31/439 (2006.01)
A61K 31/74 (2006.01)
A61K 31/215 (2006.01)
A61K 31/473 (2006.01)
A61K 31/4745 (2006.01)
A61K 9/00 (2006.01)

(52) U.S. Cl.
CPC ............. *A61K 9/0019* (2013.01); *A61K 9/0024* (2013.01); *A61K 31/74* (2013.01); *A61K 31/215* (2013.01); *A61K 31/473* (2013.01); *A61K 31/4745* (2013.01)
USPC .......................................... 514/295; 424/450

(58) Field of Classification Search
USPC .......................................... 514/295; 424/450
See application file for complete search history.

(56) References Cited

U.S. PATENT DOCUMENTS

| | | | |
|---|---|---|---|
| 4,776,353 A | 10/1988 | Lilja et al. | |
| 4,839,174 A | 6/1989 | Baker et al. | |
| 4,848,376 A | 7/1989 | Lilja et al. | |
| 4,907,606 A | 3/1990 | Lilja et al. | |
| 4,908,213 A | 3/1990 | Govil et al. | |
| 4,929,731 A | 5/1990 | Kozikowski et al. | |
| 4,943,435 A | 7/1990 | Baker et al. | |
| 4,967,773 A | 11/1990 | Shaw | |
| 5,004,610 A | 4/1991 | Osborne et al. | |
| 5,035,252 A | 7/1991 | Mondre | |
| 5,104,880 A | 4/1992 | Kozikowski | |
| 5,106,979 A | 4/1992 | Kozikowski et al. | |
| 5,147,654 A | 9/1992 | Place et al. | |
| 5,177,082 A | 1/1993 | Yu et al. | |
| 5,230,896 A | 7/1993 | Yeh et al. | |
| 5,293,883 A | 3/1994 | Edwards | |
| 5,326,563 A | 7/1994 | Spindler et al. | |
| 5,364,630 A | 11/1994 | Osborne et al. | |
| D358,683 S | 5/1995 | Bianco | |
| 5,411,739 A | 5/1995 | Jaeger et al. | |
| 5,547,960 A | 8/1996 | Kozikowski et al. | |
| 5,549,906 A | 8/1996 | Santus | |
| 5,603,947 A | 2/1997 | Wong et al. | |
| 5,633,008 A | 5/1997 | Osborne et al. | |
| 5,662,920 A | 9/1997 | Santus | |
| 5,663,344 A | 9/1997 | Kozikowski et al. | |
| 5,716,635 A | 2/1998 | Cody | |
| 5,725,876 A | 3/1998 | Mantelle et al. | |
| 5,799,633 A | 9/1998 | Miller | |
| 5,869,672 A | 2/1999 | Kozikowski et al. | |
| 5,908,213 A | 6/1999 | Tippetts et al. | |
| 5,929,084 A | 7/1999 | Zhu et al. | |
| 5,939,100 A | 8/1999 | Albrechtsen et al. | |
| 5,943,435 A | 8/1999 | Gaborski | |
| 6,083,962 A | 7/2000 | Rose et al. | |
| 6,358,941 B1 | 3/2002 | Snorrason et al. | |
| RE38,460 E | 3/2004 | Zhu et al. | |
| 2003/0158147 A1 | 8/2003 | Yerxa et al. | |
| 2004/0214863 A1 | 10/2004 | Pratt | |
| 2005/0065176 A1 | 3/2005 | Field et al. | |
| 2005/0129783 A1 | 6/2005 | McCleary et al. | |
| 2005/0222123 A1 | 10/2005 | Tracey et al. | |

(Continued)

FOREIGN PATENT DOCUMENTS

CN 1709508 A 12/2005
WO WO-2005027975 A1 3/2005

(Continued)

OTHER PUBLICATIONS

Giblin, Is Epilepsy a Preventable Disorder? New Evidence form Animal Models, neuroscientist, Jun. 2010, 16(3); pp. 1-36.*
Temkin in the abstract (Antiepileptogenic Agents, Drugs 2001: 61 (8), pp. 1045-1055, abstract only).*
Lallement et al. "Efficacy of Huperzine in Preventing Soman-Induced Seizures, Neuropathological Changes and Lethality." *Fundam. Clin. Pharmacol.* 11(1997):387-394.
"Huperzine A." *Drugs R&D.* 5.1(2004):44-45.
Attal et al. "EFNS Guidelines on Pharmacological Treatment of Neuropathic Pain." *Eur. J. Neurol.* 13(2006):1153-1169.
Ayer et al. "Alkaloids of *Lycopodium selago.*" *Can. J. Chem.* 67.10(1989):1538-1540.
Ayer et al. "Some new *Lycopodium* Alkaloids." *Can. J. Chem.* 67.6(1989):1077-1086.
Barton et al. "Pharmacological Characterization of the 6 Hz Psychomotor Seizure Model of Partial Epilepsy." *Epilep. Res.* 47.3(2001):217-227.

(Continued)

*Primary Examiner* — San-Ming Hui
*Assistant Examiner* — Kathrien Cruz
(74) *Attorney, Agent, or Firm* — Mintz Levin Cohn Ferris Glovsky and Popeo, P.C.; Ingrid A. Beattie; Linyu L. Mitra

(57) ABSTRACT

Methods and compositions containing huperzine are used to prevent and alleviate seizures. The invention is also directed to methods and compositions for using huperzine for the prevention and/or treatment of orthostatic hypotension.

31 Claims, 3 Drawing Sheets

(56) References Cited

U.S. PATENT DOCUMENTS

| | | |
|---|---|---|
| 2006/0194723 A1 | 8/2006 | Rabinoff |
| 2006/0264455 A1 | 11/2006 | Schachter |
| 2007/0281961 A1 | 12/2007 | Reynolds |
| 2008/0064694 A1 | 3/2008 | Heil et al. |
| 2008/0090808 A1 | 4/2008 | Volvovitz |
| 2008/0119506 A1 | 5/2008 | Zhang |
| 2009/0048234 A1 | 2/2009 | Volvovitz |

FOREIGN PATENT DOCUMENTS

| | | |
|---|---|---|
| WO | WO-2005102268 A2 | 11/2005 |
| WO | WO-2006127748 A1 | 11/2006 |
| WO | WO-2007014498 A1 | 2/2007 |

OTHER PUBLICATIONS

Bieri et al. "The Faces Pain Scale for the Self-Assessment of the Severity of Pain Experienced by Children: Development, Initial Validation, and Preliminary Investigation for Ratio Scale Properties." *Pain*.41.2(1990):139-150.

Block et al. "Glutamatantogonisten bei Neuropathischen Schmerzen." *Schmerz*. 17.4(2003):261-267. (German Language Article Only).

Bromfield. "Diagnosis and Classification of Epilepsy." *Office Prac. Neurol.* Samuels et al., ed. Philadelphia: Churchill Livingstone Press. Ch. 145-146(2003):928-937.

Brufani et al. "Rational Design of New Acetylcholinesterase Inhibitors." *Alzheimer Disease: From Molecular Biology to Therapy*. Becker et al., eds. Boston: Birkhäuser. (1996):171-177.

Cahn et al. "Specification of Configuration About Quadricovalent Asymmetric Atoms." *J. Chem. Soc*. (1951):612-622.

Cahn et al. "Specification of Molecular Chirality." *Agnew. Chem. Inter. Edit*.5.4(1966):385-410.

Cahn et al. "Spezifikation der Molekularen Chiralitat." *Agnew. Chem.* 78.8(1966):413-447.

Cahn et al. "The Specification of Asymmetric Configuration in Organic Chemistry." *Experientia*. 12.3(1956):81-124.

Cahn. "An Introduction to the Sequence Rule." *J. Chem. Educ.* 41.3(1964):116-125.

Colombo et al. "Medications for Neuropathic Pain: Current Trends." *Neurol.* 27.S2(2006):S183-S189.

Ebert et al. "Opiod Analgesics as Noncompetitive N-Methyl-D-Aspartate (NMDA) Antagonists." *Biochem. Pharmacol.* 56.5(1998):553-559.

Feng et al. "Synthesis and Acetylcholinesterase Inhibition of Derivatives of Huperzine B." *Bioorg. Med. Chem. Lett*. 15.3(2005):523-526.

Freeman. "Newer Agents for the Treamtent of Painful Diabetic Peripheral Neuropathy." *Curr. Diab. Rep.* 5.6(2005):409-416.

Galetotti et al. "Antinociceptive Profile of the Natural Cholinesterase Inhibitor Huperzine A." *Drug Dev. Res.* 54.1(2001):19-26.

Giacobini. "Cholinesterase Inhibitors Do More Than Inhibit Cholinesterase." *Alzheimer Disease: From Molecular Biology to Therapy*. Becker et al., eds. Boston: Birkhäuser. (1996):187-204.

Gilron et al. "Neuropathic Pain: A Practical Guide for the Clinician." *CMAJ.* 175.3(2006):265-275.

Goddard et al. "A Permanent Change in Brain Function Resulting From Daily Electrical Stimulation." *Exp. Neurol.* 25.3(1969):295-330.

Gordon et al. "The NMDA Receptor Ion Channel: A Site for Binding of Huperzine A." *J. Appl. Toxicol*. 21.S1(2001):S47-S51.

Greig et al. "Phenserine: A Selective, Long-Acting and Brain-Directed Acetylcholinesterase Inhibitor Affecting Cognition and β-APP Processing." *Alzheimer Disease: From Molecular Biology to Therapy*. Becker et al., eds. Boston: Birkhäuser. (1996):231-237.

Hewitt. "The Use of NMDA-Receptor Antagonists in the Treatment of Chronic Pain." *Clin. J. Pain*.16.S(2000):S73-S79.

Hunskaar et al. "Formalin Test in Mice, A Useful Technique for Evaluation Mild Analgesics." *J. Neurosci. Meth*. 14.1(1985):69-76.

Jiang et al. "Progress in Clinical, Pharmacological, Chemical and Structural Biological Studies of Huperzine A: A Drug of Traditional Chinese Medicine Origin for the Treatment of Alzheimer's Disease." *Curr. Med. Chem.* 10.21(2003):2231-2252.

Klitgaard et al. "Antiepileptogenesis, Neuroprotection, and Disease Modification in the Treatment of Epilepsy: Focus on Levetiracetam." *Epileptic Disord*. 5.S1(2003):S9-S16.

Kuttner et al. "Face Scales for the Assessment of Pediatric Pain: A Critical Review." *Can. J. Behav. Sci*.21.2(1989):198-209.

Liu et al. "The Structures of Huperzine A and B, Two New Alkaloids Exhibiting Marked Anticholinesterase Activity." *Can. J. Chem*.64.4(1986):837-839.

Ma et al. "Double-Blind Trial of Huperzine-A (HUP) on Cognitive Deterioration in 314 Cases of Benign Senescent Forgetfulness, Vascular Dementia, and Alzheimer's Disease." *Ann. N.Y. Acad. Sci.* 854(1998):506-507.

Ma et al. "Double-Blind Trial of Huperzine-A (HUP) on Cognitive Impairment and Dementia in 314 Cases." *N-S Arch. Pharmacol*.358.1(1998):R76. (Abstract P 35.194).

Ma et al. "The Lycopodium Alkaloids." *Nat. Prod. Rep.* 21(2004):752-772.

Max. "Neuropathic Pain Syndromes." *Adv. Pain Res. Ther.* 18(1991):193-219.

McKhann et al. "Clinical Diagnosis of Alzheimer's Disease: Report of the NINCDS-ADRDA Work Group Under the Auspices of Department of Health and Human Services Task Force on Alzheimer's Disease." *Neurol.* 34.7(1984):939-944.

Meldrum. "Implications for Neuroprotective Treatments." *Prog. Brain Res.* 135(2002):487-495.

Melzack. "The McGill Pain Questionnaire: Major Properties and Scoring Methods." *Pain*. 1.3(1975):277-299.

Parsons. "NMDA Receptors as Targets for Drug Action in Neuropathic Pain." *Eur. J. Pharmacol*.429(2001):71-78.

Peyron. "Intraarticular Hyaluronan Injections in the Treatment of Osteoarthritis: State-of-the-Art-Review." *J. Rheumatol.* 20.S39(1993):10-15.

Proudfoot et al. "Analgesia Mediated by the TRPM8 Cold Receptor in Chronic Neuropathic Pain." *Curr. Biol*. 16.16(2006):1591-1605.

Pud et al. "The NMDA Receptor Antagonist Amantadine Reduces Surgical Neuropathic Pain in Cancer Patients: A Double Bind, Randomized, Placebo Controlled Trial." *Pain*.75(1998):349-354.

Pud et al. *Harefuah*. 136.7(1999):564-567. (Hebrew Language Article Only).

Rajendran et al. "Synthesis of More Potent Analogues of the Acetylcholinesterase Inhibitor, Huperzine B." *Bioorg. Med. Chem. Lett*. 12(2002):1521-1523.

Salter. "Cellular Neuroplasticity Mechanisms Mediating Pain Persistence." *J. Orofac. Pain*. 18.4(20040:318-324.

Sang. "NMDA-Receptor Antagonists in Neuropathic Pain: Experimental Methods to Clinical Trials." *J. Pain Symptom Manage.* 19.S1(2000):S21-S25.

Sarkisian. "Overview of the Current Animal Models for Human Seizure and Epileptic Disorders." *Epilep. Behav*. 2.3(2001):201-216.

Sato et al. "An Analysis of Anticonvulsant Actions of GABA Agonists (Progabide and Baclofen in the Kindling Model of Epilepsy." *Epilep. Res.* 5.1(1990):117-124.

Schachter. "Epilepsy." *Saunders Manual of Neurologic Practice*. Evans, ed. Philadelphia: Saunders. Part VII(2003):2447-255.

Schmidt et al. "Preclinical Pharmacology of Metrifonate: A Promise for Alzheimer Therapy." *Alzheimer Disease: From Molecular Biology to Therapy*. Becker et al., eds. Boston: Birkhäuser. (1996):216-221.

Silver et al. "Antieplileptogenic Effects of Conventional Anticonvulsants in the Kindling Model of Epilepsy." *Ann. Neurol.* 29.4(1991):356-363.

Singer et al. "Acetylcholinesterase Inhibition: A Novel Approach in the Treatment of Neurogenic Orthostatic Hypotension." *J. Neurol. Neurosurg. Psych*. 74.9(2003):1294-1298.

Sittl et al. "Transdermal Buprenorphine in Cancer Pain and Palliative Care." *Palliat. Med.* 20.S1(2006):S25-S30.

Sun et al. "Huperzine-A Capsule Enhance Memory and Learning Performance in 34 Pairs of Matched Adolescent Students." *Acta Pharmacol. Sin*. 20.7(1999):601-603.

(56) References Cited

OTHER PUBLICATIONS

Temkin et al. "Antiepileptogenic Agents: How Close Are We?" *Drugs*. 61.8(2001):1405-1055.

Tonduli et al. "Effects of Huperzine Used as Pre-Treatment Against Soman-Induced Seizures." *Neurotoxicol*. 22.1(2001):29-37.

Vargas et al. "P11467: An Orally-Active Acetylcholinesterase Inhibitor and $\alpha_2$-Adrenceptor Antagonist for Alzheimer's Disease." *Alzheimer Disease: From Molecular Biology to Therapy*. Becker et al., eds. Boston: Birkhäuser. (1996):254-255.

Wada et al. "Persistent Seizure Susceptibility and Recurrent Spontaneous Seizures in Kindled Cats." *Epilepsia*. 15(1974):465-478.

Walker. "Attention Baby Boomers." *Better Nut*. 61.9(1999):1-2.

Wang et al. "Comparison of the Effects of Cholinesterase Inhibitors of [$^3$H]MK-801 Binding in Rat Cerebral Cortex." *Neurosci. Lett*. 272.1(1999):21-24.

Ward et al. "A Radical Mediated Approach to the Core Structure of Huperzine A." *Tetrahed. Lett*. 47(2006):553-556.

Weber. "NMDA-Rezeptorantagonisten in der Schmerztherapie." *Anasthesiol. Intensivmed. Notfallmed. Schmerzher*. 33.8(1998):475-483. (German Language Article with English Abstract).

Wright et al. "Factorial Validity of the Short-Form McGill Pain Questionnaire (SF-MPQ)." *Eur. J. Pain*. 5.3(2001):279-284.

Xu et al. "Efficacy of Tablet Huperzine-A on Memory, Cognition, and Behaviour in Alzheimer's Disease." *Acta Pharmacol. Sin*. 16.5(1995):391-395.

Xu et al. "Huperzine-A in Capsules and Tablets for Treating Patients with Alzheimer's Disease." *Acta Pharmacol. Sin*. 20.6(1999):486-490.

Yan et al. "Effects of Hupezine A and B on Skeletal Muscle and Electro-Encephalogram." *Acta Pharmacol. Sin*. 8.2(1987):117-123. (Chinese Language Article with English Abstract).

Ye et al. "Huperzine A Ameliorates the Impaired Memory of Aged Rat in the Morris Water Maze Performance." *Acta. Pharmacol. Sin*. 21.1(2000):65-69.

Ye et al. "Improving Effects of Huperzine A on Spatial Working Memory in Aged Monkeys and Young Adult Monkeys With Experimental Cognitive Impairment." *J. Pharmacol. Exp. Therpeut*. 288. 2(1998):814-819.

Zhang et al. "Clinical Efficacy and Safety of Huperzine $\alpha$ in Treatment of Mild to Moderate Alzheimer Disease, a Placebo-Controlled, Double-Blind, Randomized Trial." *Zhonghua Yi Xue Za Zhi*. 82.14(2002):941-944. (English Abstract Only).

Zhou et al. "Huperzine A Attenuates Cognitive Deficits and Hippocampal Neuronal Damage After Transient Glocal Ischemia in Gerbils." *Neurosci. Lett*. 313.3(2001):137-140.

* cited by examiner

USE OF HUPERZINE FOR DISORDERS

RELATED APPLICATIONS

This application is a continuation of U.S. Ser. No. 12/779,612, now U.S. Pat. No. 8,093,262, filed May 13, 2010, which is a continuation of U.S. Ser. No. 11/439,557, filed May 23, 2006 and claims the benefit of U.S. Ser. No. 60/683,745, filed May 23, 2005, and U.S. Ser. No. 60/756,141, filed Jan. 4, 2006, respectively. The contents of each provisional application are hereby incorporated by reference.

BACKGROUND OF THE INVENTION

The technical field of this invention relates to using NMDA antagonists and acetylcholinesterase (AChE) inhibitors in neurologic syndromes and disorders.

Pain management remains a ubiquitous clinical problem. In addition to injury, nearly every disease or pathological condition from arthritis to cancer to HIV infection and diabetes has a major pain component. Pain management for some conditions such as nerve injuries and chronic inflammatory disease has been poor. While a number of drugs exist to alleviate pain, the use of many of them is limited by safety issues and side effects.

SUMMARY OF THE INVENTION

Huperzine has been found to be useful to reduce the severity and perception of pain as well as to reduce the severity or duration of a neurologic disorder such as a seizure disorder. A purified huperzine compound or an analogue thereof that interferes with an action of an excitatory amino acid at the N-methyl-D-aspartate (NMDA) receptor is administered to a subject that has been diagnosed as suffering from or at risk of developing such one or more of such conditions. Huperzine compounds are used to treat both acute and chronic pain indications. Major categories of pain to be treated include post-operative and post trauma pain; non-malignant chronic pain disorders such as osteoarthritis and rheumatoid arthritis, fibromyalgia, multiple sclerosis and headache; neuropathic pain such as that associated with peripheral nerve damage, diabetes, and Human Immunodeficiency Virus (e.g., HIV-1, AIDS) infection; back pain such as that associated with disc avulsion or nerve compression; and cancer pain, including pain secondary to chemotherapy. Neuropathic pain includes chronic pain resulting from injury to the nervous system, e.g., an injury to the central nervous system (brain and spinal cord) or the peripheral nervous system (nerves outside the brain and spinal cord). In some cases, neuropathic pain occurs after trauma and is associated with pathologic conditions such as multiple sclerosis and stroke. Neuropathic pain is also associated with shingles (post-herpetic neuralgia due to Varicella-zoster virus).

A method of reducing pain perception is characterized by identifying a subject with an injury and administering to the individual an amount of a huperzine compound sufficient to reduce pain perception by at least 10% compared to the level of pain perception in the absence of a medicament. Preferably, perception of pain is reduced by at least 20%, 50%, 75%, eliminated or rendered imperceptible by the patient. In one example, the subject has been diagnosed with an injury to a bodily tissue or inflammation of a bodily tissue. For example, the injury is a cut, bruise, fracture, crush injury or is the result of a surgical procedure. The subject is identified as experiencing pain related to passage of kidney stones, a dental extraction, caesarian surgery, or cancer. Preferably, the subject is distinguished from a subject suffering from Alzheimer's Disease (AD). For example, the subject is less than 70 years of age. In another example, the subject does not meet the National Institute of Neurological Disorders and Stroke (NINDS)/Alzheimer's Disease and Related Disorders Association (ADRDA) (collectively, NINDS/ADRDA) criteria for probable AD. The subject is characterized as having a score of at least 27 on a MMSE. Alternatively, the subject is diagnosed with both AD and pain. Such patients are also treated using a huperzine compound; however, the dose and mode of administration of the compound is different for AD compared to pain. For example, administration for pain is preferably carried out using a sustained release formulation.

Alternatively, the subject is identified as experiencing pain in the absence of an injury or inflammation of a bodily tissue. A purified huperzine compound is administered to the individual as described above in an amount of a huperzine compound sufficient to reduce pain perception by at least 10% compared to the level of pain perception in the absence of a medicament. Examples of such pain syndromes include patients identified as suffering from neuropathic pain, e.g., neuropathic pain associated with diabetes or HIV infection.

A method for preventing, reducing the severity, frequency, or duration of a seizure is carried out by identifying a subject suffering from or at risk of developing a seizure disorder; and administering to the subject a composition containing a purified huperzine compound. As above, the subject is distinguished from a subject suffering from Alzheimer's Disease (AD). The subject is diagnosed with epilepsy or is diagnosed with both epilepsy and AD (e.g., the subject has a score of less than 27 on a Mini Mental State Examination (MMSE)).

Huperzine confers clinical benefit to individuals afflicted with other pathological disorders. For example, a subject is identified as suffering from or at risk of developing orthostatic hypotension or Reflex Sympathetic Dystrophy Syndrome (RSD)/Complex Regional Pain Syndrome (CRPS). The latter syndrome is a chronic neurological syndrome characterized by one or more of the following symptoms: severe burning pain, pathological changes in bone and skin, excessive sweating, tissue swelling, or extreme sensitivity to touch. Reduction in pain is measured using standard medical methods of evaluating and scoring pain, e.g., the McGill Pain Questionnaire.

Huperzine compounds are administered at a dose to reduce pain or seizures by at least 10% with few or no side effects. Preferably, the reduction is 20%, 50%, 75% or eliminates pain or seizure episodes. For example, the huperzine compound prevents the development of or completely eliminates pain or seizures. The dose preferably does not exceed 20 mg/kg of body weight/day. For example, the dose does not exceed 10 mg/kg/day. In exemplary treatment protocols, the dose is less than 0.83 mg/kg/day such as a dose of between 0.1 and 0.5 mg/kg/day or a dose of between 0.2 and 0.3 mg/kg/day. Mode of administration is oral, intravenous, subcutaneous, or topical. Topical administration, e.g., in the form of a cream, foam, or ointment, is useful to alleviate neuropathic pain associated with shingles.

Compounds useful in the methods of the invention include compounds of Formula I:

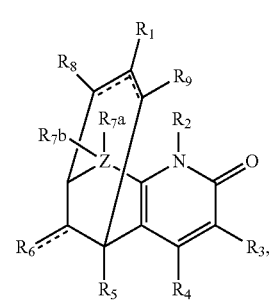

where:

$R_1$ is hydrogen, C1-C8 alkyl, halo, pyridoyl, or benzoyl substituted by C1-C5 lower alkoxy or C1-C5 alkyl-OH;

$R_2$ is hydrogen, C1-C8 alkyl, or halo;

$R_3$ is hydrogen, C1-C8 alkyl, halo, $NO_2$, or OH;

$R_4$ is hydrogen, C1-C8 alkyl, halo, $NO_2$, or OH;

$R_5$ is $CO_2R'$, where R' is H, (C1-C4)alkyl or phenyl, optionally substituted by one or two X, wherein X is halo, $CF_3$, $OR_{12}$, $SR_{12}$, CN, $NO_2$, $CO_2R_{12}$, $C(O)N(R_{12})_2$, $S(O)R_{12}$ or $SO_2R_{12}$, wherein each $R_{12}$ is H, $CF_3$, phenyl or (C1-C4)alkyl;

or $R_5$ is $(CH_2)_pNR_aR_b$, where p is 0 or 1 and $R_a$ and $R_b$ are individually H, (C1-C8)alkyl, aryl, aralkyl, or one of $R_a$ and $R_b$ is —CH=CH-G, where G is phenyl, furanyl, naphthyl, pyridyl, or dihydro or tetrahydropyridyl substituted by C1-C5 alkyl at the nitrogen atom, and G is optionally substituted with 1, 2, or 3 B, where B is C1-C5 alkyl; C1-C5 alkoxy; C1-C5 alkyl-OH; nitro; halo; carboxy; alkyloxycarbonyl; hydroxymethyl; hydroxy; amino, or amino substituted by bis-C1-C5 alkyl (the alkyl groups may be the same or different), and the other of $R_a$ and $R_b$ is hydrogen or (C1-C8)alkyl; or one of $R_a$ and $R_b$ is $C(O)R_{14}$ and the other of $R_a$ and $R_b$ is $R_{15}$, where $R_{14}$ is (C1-C8)alkyl, $—(CH_2)_qCOOY$, where q is 0, 1, 2, 3, 4, or 5 and Y is hydrogen or C1-C5 alkyl; $(CH_2)_m$-G where m is 0 or 1 and G is phenyl, furanyl, naphthyl, pyridyl, or dihydro or tetrahydropyridyl substituted by C1-C5 alkyl at the nitrogen atom, and G is optionally substituted with 1, 2, or 3 B, where B is C1-C5 alkyl; C1-C5 alkoxy; C1-C5 alkyl-OH; nitro; halo; carboxy; alkyloxycarbonyl; hydroxymethyl; hydroxy; amino, or amino substituted by bis-C1-C5 alkyl (the alkyl groups may be the same or different); $R_{15}$ is hydrogen or (C1-C8)alkyl; or or $R_5$ is $(CH_2)_pN=R_{16}$, where $R_{16}$ is $CH(CH_2)_m$-G, where m is 0 or 1 and G is phenyl, furanyl, naphthyl, pyridyl, or dihydro or tetrahydropyridyl substituted by C1-C5 alkyl at the nitrogen atom G is optionally substituted with 1, 2, or 3 B, where B is C1-C5 alkyl; C1-C5 alkoxy; C1-C5 alkyl-OH; nitro; halo; carboxy; alkyloxycarbonyl; hydroxymethyl; hydroxy; amino, or amino substituted by bis-C1-C5 alkyl (the alkyl groups may be the same or different);

$R_6$ is $CR_cR_dR_e$, where $R_1$ is H, halo or (C1-C8)alkyl, $R_d$ is halo or (C1-C8)alkyl; $R_e$ is H or is absent when a double bond is present;

one of $R_{7a}$ and $R_{7b}$ is hydrogen or (C1-C8)alkyl and the other of $R_{7a}$ and $R_{7b}$ is hydrogen, (C1-C8)alkyl, vinyl, (C3-C8)alkenyl, ethynyl, CN, $NO_2$, halo, OR', SR', $CO_2R'$, $C(O)N(R)_2$, C(O)R', S(O)R' or $SO_2R'$, wherein R' is H, (C1-C4) alkyl or phenyl, optionally substituted by 1 or 2 X, wherein X is halo, $CF_3$, $OR_{12}$, $SR_{12}$, CN, $NO_2$, $CO_2R_{12}$, $C(O)N(R_{12})_2$, $S(O)R_{12}$ or $SO_2R_{12}$, wherein each $R_{12}$ is H, $CF_3$, phenyl or (C1-C4)alkyl; or $R_{7a}$ and $R_{7b}$ together are connected to form carbonyl (=O) or $=C(R_{10})(R_{11})$ wherein each of $R_{10}$ and $R_{11}$ is H, X or (C1-C4)alkyl;

optionally $R_5$ and $R_6$ are connected to form a saturated 6, 7, or 8 membered ring, optionally containing 1 or 2 heteroatoms selected from O, $NR_{13}$, and S, where $R_{13}$ is hydrogen or C1-C8 alkyl;

$R_8$ is hydrogen, C1-C8 alkyl, or hydroxyl;

$R_9$ is hydrogen, C1-C8 alkyl, or hydroxyl;

Z is $(CH_2)_n$, where n is 1, 2, 3, or 4;

C1-C8 alkyl includes both linear and branched alkyl, and where a dashed line indicates the presence or absence of a double bond, as consistent with the laws of chemical bonding, with the proviso that if a double bond is present between $CR_1$ and $CR_9$, then there is no double bond between $CR_1$ and $CR_8$, or f a double bond is present between $CR_1$ and $CR_8$, then there is no double bond between $CR_1$ and $CR_9$.

The invention includes the use of isomers, tautomers, polymorphs, solvates and hydrates of compounds of Formula I as well as the use of the pharmaceutically acceptable salts of compounds of Formula I. For example, the salt can be an acid addition salt. One example of an acid addition salt is a hydrochloride salt.

In compounds of Formula I, when $R_1$ is $CH_3$; $R_2$, $R_3$, $R_4$, $R_{7a}$, $R_{7b}$, $R_8$ and $R_9$ are hydrogen; $R_6$ is $CHCH_3$ (the double bond is present); $R_5$ is $(CH_2)_pNR_aR_b$, where p is 0, $R_a$ and $R_b$ are H; and the double bond is present between $CR_8$ and $CR_1$, then the compound is Huperzine A.

In compounds of Formula I, when $R_1$ is $CH_3$; $R_2$, $R_3$, $R_4$, $R_{7a}$, $R_{7b}$, $R_8$ and $R_9$ are hydrogen; the double bond is present between $CR_8$ and $CR_1$, $R_5$ and $R_6$ are connected to form a 6 membered piperidine ring, then the compound is Huperzine B.

Huperzine compounds are extracted from plants or are chemically synthesized. In either case, the compound is purified from compositions with which it naturally occurs. Preferably, the compound is at least 98%, 99%, or 100% (w/w) of the huperzine compound or analogue thereof by weight. Purity is assessed by any known method, e.g., high performance liquid chromatography (HPLC).

Huperzine compounds include huperzine A and/or B as described above and analogs thereof. The huperzine compounds are administered alone or in combination with one another. The formulations do not contain nutritional supplements such as Gingko biloba or vitamins (e.g., Vitamin E). Analogues interfere with action of excitatory amino acids at the NMDA receptor and possess the activity of pain prevention and reduction as well as prevention or reduction in the duration, frequency, or severity of a seizure. Huperzine A analogues are characterized as interacting with the same or adjacent site in the active site of the acetylcholinesterase enzyme as Huperzine A.

A composition containing a purified huperzine compound is formulated in a sustained release delivery vehicle. The vehicle includes dermal patch, an intravenous pump, or another implantable device. The implant is inert, biodegradable, or erodible. For sustained release in an implant, patch, or oral composition, the vehicle contains a semipermeable membrane. The membrane serves the purpose of controlling the rate of delivery of the huperzine compound to bodily tissues. In another example of a sustained release formulation, the vehicle contains a a plurality particles, each of which are characterized as having a different rate of dissolution. For example, a composition may contain two or more classes of particles: slow, medium, and rapid release particles. A dosing regimen contains one or more doses of a sustained release formulation as needed to manage pain or reduce the frequency, severity, or duration of seizures. Alternatively, one or more high doses (5, 10, 15, 20, or 30 mg/kg/day are administered followed by lower doses (0.1-5 mg/kg/day) for management of symptoms. Other formulations include an ointment, paste, spray, patch, cream, gel, resorbable sponge, foam, or subcutaneous depo formulation.

Administration is prior to, during, or after the onset of a seizure or pain. Huperzine, e.g., huperzine A (Hup A), huperzine B (Hup B), or combinations thereof, is used for the treatment and/or prevention of epilepsy and seizures. Huperzine can also be used to treat or prevent disorders associated with the N-methyl-D-aspartate (NMDA) receptor. Huperzine can also be used to treat or prevent disorders associated with aberrant acetylcholine levels.

Subjects to be treated are diagnosed and distinguished from those patients with AD. For example, MMSE scores of 27 and above are considered normal; scores of between 23 and 26 indicate a borderline condition; scores of 22 and below are abnormal; scores 20 to 26 equal to mild AD; scores of 10 to 19 equal to moderate AD; and, scores below 10 indicate severe AD The invention pertains to a method for treating or preventing orthostatic hypotension in a subject, such as that which occurs in subjects with migraine headaches, by administering a substantially purified huperzine. The huperzine inhibits acetylcholinesterase activity, to thereby treat or prevent orthostatic hypotension in the subject. Huperzine compounds are also useful to prevent and reduce the occurrence, duration or frequency of other conditions associated with dizziness such as idiopathic vertigo. In neurogenic causes of orthostatic hypotension, huperzine compounds interfere with the action of excitatory amino acids at the NMDA receptor as a neuroprotective mechanism.

Neurodegeneration can occur in any area of the brain of a subject and is seen with many disorders including, for example, epilepsy, head trauma, stroke, amyotrophic lateral sclerosis (ALS; Lou Gehrig's disease), multiple sclerosis, Huntington's disease, Parkinson's disease, and Alzheimer's disease. Huperzine is useful to reduce the severity of ALS.

Huperzine compounds are also useful to prevent and reduce the severity of post-operative cognitive difficulties such as those associated with cardiac bypass surgery. This condition involves overstimulation of NMDA receptors in the brain with glutamate. A huperzine compound is administered as a neuroprotective agent in the context of a patient undergoing this operation. For example, the patient is administered a huperzine compound for a period of time prior to the operation (e.g., 24, 12, 8, 4, 2, 1 hour prior to surgery). Optionally, administration is continued for a period of time after surgery (e.g., 1, 2, 4, 8, 12, 24, 48, 96 hours after surgery) or until cognitive difficulties diminish or are eliminated.

The term "seizure" as used herein refers to a change in behavior, or spasms or convulsions that arise naturally in a subject as a result of a natural chemical imbalance or lack of homeostasis in a subject. Such natural convulsions may arise due to a disease or disorder (e.g., epilepsy), age, or the occurrence of an event (e.g., stroke). The term "seizure" also refers to seizures that are chemically induced, for example those brought on by intake, uptake, or ingestion of chemicals such as organophosphates.

The term "antiepileptogenic" refers to inhibiting at least one of the processes that underlie the development of epilepsy.

The term "neuropathic pain" refers to the art recognized use of the term for pain which does not respond conventionally to opiate drugs such as morphine. Huperzine and its analogs can be used to alleviate, suppress or inhibit the existing pain, as well as prevent pain from arising from a pain-causing event or disorder.

The term "orthostatic hypotension" is often defined as a fall in blood pressure of at least 20 mm Hg systolic or 10 mm Hg diastolic within three minutes in the upright position. It can also be generally characterized by dizziness, light-headedness, visual blurring, and fainting when a person assumes a standing position. Huperzine and its analogs can be used to alleviate, suppress or inhibit the orthostatic hypotension, as well as prevent orthostatic hypotension from arising in patients at risk.

The term "treatment" or "treating" refers to a decrease in the symptoms associated with the disorder or an amelioration of the recurrence of the symptoms of the disorder, prophylaxis, or reversal of a disease or disorder, or at least one discernible symptom thereof. The term "treatment" or "treating" refers to inhibiting or slowing the progression of a disease or disorder, e.g., epilepsy, physically, e.g., stabilization of a discernible symptom, such as seizures. The term "treatment" or "treating" refers to delaying the onset of a disease or disorder, e.g., seizures. These terms also refer to suppressing, reducing or inhibiting pain, such as neuropathic pain. These terms also refer to suppressing, reducing or inhibiting orthostatic hypotension.

The term "prevention" or "preventing" refers to delaying the onset of the symptoms of the disorder. Huperzine is administered as a preventative measure to a subject having a genetic or non-genetic predisposition to a neurological disorder such as epilepsy. In another embodiment, the huperzine is administered as a preventative measure for a subject at risk of developing seizures as a result of another medical event. For example, patients who have a suffered a stroke are often at risk of developing seizures. In these instances, the huperzine can be administered after the stroke as a preventative measure against seizures. These terms also refer to preventing the onset of pain, such as neuropathic pain. These terms also refer to preventing the onset of orthostatic hypotension.

The term "neuroprotection" or "neuroprotective activity" as used herein refers to treating or preventing seizures associated with epilepsy or seizures arising from some other disorder or ailment, such as stroke. This term also refers to protection against pain such as neuropathic pain or hypotension such as a orthostatic hypotension.

Other embodiments are described in the description. All references cited herein are hereby incorporated by reference.

DETAILED DESCRIPTION

Figure 1:
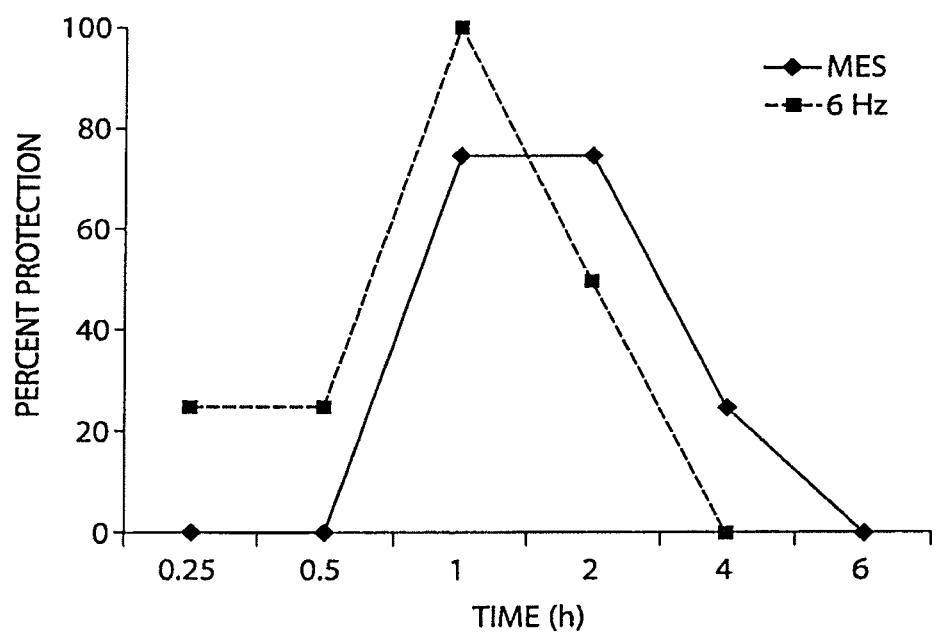
FIG. 1 is a line graph showing that Huperzine A displays time-dependent protection in the mouse MES and 6 Hz tests following administration of 1 and 0.8 mg/kg of the compound.

Pain is diagnosed and evaluated in a number of standard methods such as the McGill Questionnaire (Melzack, R., 1975, Pain 1:277-299; Wright et al, 2001, Eur. J. Pain 5:279-284). Children as young as two years old can report pain, and standards for evaluating pain in children include evaluation of facial expression (Bieri et al., 1990, Pain 41: 139-150; Kuttner et al, 1989, Can. J. Behav. Sci. 21: 198-209). A medically desirable result of a reduction in pain for joint disease such as osteoarthritis is measured, e.g., using a visual analog pain scale described in Peyron et al., 1993, J. Rheumatol. 20 (suppl.39):10-15).

Huperzine compounds are used to relieve both acute and chronic pain. Subjects to be treated are diagnosed with pain as described above or report/describe pain perception. Administration for pain relief is distinguished from patients or mode of administration for treatment of AD. For example, candidate patients for treatment are selected based on exclusion from the NINCDS-ADRDA criteria for AD or probable AD (McKhann et al., 1984, Neurology 34:939-944). In another example, the dose and formulation differs from an AD treatment regimen. Huperzine administration for pain includes continuous exposure (e.g., using an implant or intravenous or spinal pump) or by sustained release using a timed release oral tablet or capsule.

Pain Reduction

Huperzine compounds have been found to reduce pain in standard animal models such as the formalin test. Other standard models of pain include the rodent sciatic ligation (chronic constriction) model and intervertebral disc degeneration model.

A standard formalin test was used to evaluate the effect of Huperzine A on pain in mice. The formalin test for antinociceptive activity is described in numerous publications, e.g., Hunskaar, S., O. B. Fasmer, and K. Hole, *J. Neurosci. Methods* 14: 69-76 (1985). The formalin test is a chemically-induced tonic pain model in which biphasic changes of nociceptive behavior are assessed and spinal/supraspinal plasticity of nociception is considered as a molecular basis for neuropathic pain particularly during the second (late) phase of the test, during which most clinically used drugs against neuropathic pain are active. The formalin test is accepted as an art recognized model of persistent clinical pain.

Male Swiss Webster NIH mice (20-30 g; Harlan, San Diego, Calif.) were used in the experiments described herein. Food was withdrawn on the day of experiment. Mice were placed in Plexiglass jars for at least 1 hour to accommodate to the environment. Following the accommodation period, mice were weighed and given either a huperzine compound administered intraperitoneal (i.p.) or oral (p.o.), or the appropriate volume of vehicle (10% Tween-80). Fifteen minutes after the i.p. dosing, and 30 minutes after the p.o. dosing mice were injected with formalin (20 μL of 5% formaldehyde solution in saline) into the dorsal surface of the right hind paw. Mice were transferred to the Plexiglass jars and monitored for the amount of time spent licking or biting the injected paw. Periods of licking and biting were recorded in 5 minute intervals for 40 minutes after the formalin injection. All experiments were done in a blinded manner. The early phase (acute) of the formalin response is measured as licking/biting between 0-5 minutes, and the late phase (inflammatory) is measured from 10-40 minutes. Differences between vehicle and drug treated groups are analyzed by one-way analysis of variance (ANOVA). A P value <0.05 is considered significant. Activity in blocking the acute and second phase of formalin-induced paw-licking activity is indicative that compounds are considered to be efficacious for acute and chronic pain.

Eight mice were weighed and given either 1 mg/kg of huperzine A administered intraperitoneal (i.p.), or the appropriate volume of vehicle (10% Tween-80). Fifteen minutes after the i.p. dosing, mice were injected with formalin (20 μL of 5% formaldehyde solution in saline) into the dorsal surface of the right hind paw. Periods of licking and biting were recorded in 5 minute intervals for 40 minutes after the formalin injection as shown below in Tables 1 and 2. All experiments were done according to the art-recognized Anticonvulsant Screening Program of the NINDS at the University of Utah. Analysis of the experiments is summarized in Table 6.

After an injection of 20 μl of 2.5% formalin into the paw, mice displayed two phases of flinching behavior. Phase 1 (acute) started with initial intense flinches occurring 1-2 min after injection, followed by a rapid decline at 5-6 min. Phase 2 (inflammatory) began after 15-20 min, with the maximal response typically observed around 20-25 min after the formalin injection. Intraperitoneal injection of huperzine A into mice (1 mg/kg) produced complete inhibition on both phase 1 (acute) and phase 2 (inflammatory) pain response as shown in Tables 4-6. Duration of paw licking in the tables below is expressed in seconds. These results support and confirm the anti-neuropathic pain activity of the huperzine A.

TABLE 1

Duration of mice paw licking (seconds) at various time points after intraperitoneal administration of vehicle (10% Tween-80) and 20 μl of 2.5% formalin injection (Control Experiment)

| Dose mg/kg | Animal # | 0 min | 5 min | 10 min | 15 min | 20 min | 25 min | 30 min | 35 min | 40 min |
|---|---|---|---|---|---|---|---|---|---|---|
| 0 | 01 | 40.00 | 29.27 | 6.14 | 15.40 | 43.62 | 51.47 | 17.33 | 15.12 | 3.91 |
| 0 | 02 | 52.00 | 22.57 | 4.52 | 3.29 | 38.61 | 46.12 | 21.73 | 8.29 | 5.88 |
| 0 | 03 | 47.00 | 13.39 | 3.05 | 0.00 | 41.31 | 45.72 | 28.14 | 12.63 | 1.65 |
| 0 | 04 | 49.00 | 19.92 | 2.01 | 0.00 | 47.74 | 26.83 | 22.41 | 8.21 | 0.00 |
| 0 | 05 | 45.00 | 7.57 | 0.00 | 12.68 | 31.18 | 52.67 | 24.16 | 6.42 | 0.00 |
| 0 | 06 | 69.00 | 6.27 | 0.00 | 30.75 | 42.11 | 58.35 | 19.35 | 10.26 | 0.00 |
| 0 | 07 | 43.00 | 11.24 | 4.81 | 11.12 | 42.16 | 44.63 | 21.16 | 11.12 | 1.39 |
| 0 | 08 | 48.00 | 19.32 | 7.22 | 0.00 | 48.29 | 41.37 | 22.24 | 6.21 | 5.63 |

TABLE 2

Duration of mice paw licking (seconds) at various time points after intraperitoneal administration of 1 mg/kg huperzine A and 20 μl of 2.5% formalin injection

| Dose mg/kg | Animal # | 0 min | 5 min | 10 min | 15 min | 20 min | 25 min | 30 min | 35 min | 40 min |
|---|---|---|---|---|---|---|---|---|---|---|
| 1 | 01 | 0.00 | 0.00 | 0.00 | 0.00 | 0.00 | 0.00 | 0.00 | 0.00 | 0.00 |
| 1 | 02 | 0.00 | 0.00 | 0.00 | 0.00 | 0.00 | 0.00 | 0.00 | 0.00 | 0.00 |
| 1 | 03 | 0.00 | 0.00 | 0.00 | 0.00 | 0.00 | 0.00 | 0.00 | 0.00 | 0.00 |
| 1 | 04 | 0.00 | 0.00 | 0.00 | 0.00 | 0.00 | 0.00 | 0.00 | 0.00 | 0.00 |
| 1 | 05 | 0.00 | 0.00 | 0.00 | 0.00 | 0.00 | 0.00 | 0.00 | 0.00 | 0.00 |
| 1 | 06 | 0.00 | 0.00 | 0.00 | 0.00 | 0.00 | 0.00 | 0.00 | 0.00 | 0.00 |
| 1 | 07 | 0.00 | 0.00 | 0.00 | 0.00 | 0.00 | 0.00 | 0.00 | 0.00 | 0.00 |
| 1 | 08 | 0.00 | 0.00 | 0.00 | 0.00 | 0.00 | 0.00 | 0.00 | 0.00 | 0.00 |

TABLE 3

Analysis of results of formalin tests following intraperitoneal administration of 1 mg/kg Huperzine A

| Dose mg/kg | Test | Control | Drug Treated | % of Control | S.E.M. | p Value |
|---|---|---|---|---|---|---|
| 1 | Acute | 214.3 | 0.0 | 0.0 | 0.0 | <0.01 |
| 1 | Inflammatory | 626.8 | 0.0 | 0.0 | 0.0 | <0.01 |

In the experiments described above, a dose of 1 mg/kg was used, which, while effective, is above the $TD_{50}$ in mice. The data described below was derived using a dose of 0.5 mg/kg (i.p.). Surprisingly, an impressive reduction in the time spent licking was also observed.

TABLE 4

Analysis of results of formalin tests following intraperitoneal administration

| Dose (mg/kg) | Test | Control | Drug Tested | % of Control | S.E.M | p.Value |
|---|---|---|---|---|---|---|
| 0.5 | Acute | 263.3 | 7.3 | 2.8 | 1.1 | <0.01 |
| 0.5 | Inflammatory | 707.8 | 0.0 | 0.0 | 0.0 | <0.01 |

TABLE 5

Duration of Paw Licking (Dose of 0 mg/kg = control)

Trial 1

| Dose (mg/kg) | Animal # | 0 min | 5 min | 10 min | 15 min | 20 min | 25 min | 30 min | 35 min | 40 min | 45 min | 50 min | 55 min |
|---|---|---|---|---|---|---|---|---|---|---|---|---|---|
| 0.5 | 01 | 1.00 | 0.00 | 0.00 | 0.00 | 0.00 | 0.00 | 0.00 | 0.00 | 0.00 | | | |
| 0 | 01 | 68.00 | 8.77 | 14.72 | 21.83 | 34.21 | 6.16 | 19.09 | 74.97 | 32.94 | | | |
| 0 | 02 | 59.00 | 15.90 | 10.12 | 11.88 | 20.03 | 35.34 | 49.57 | 29.07 | 0.00 | | | |
| 0.5 | 02 | 10.00 | 0.00 | 0.00 | 0.00 | 0.00 | 0.00 | 0.00 | 0.00 | 0.00 | | | |
| 0.5 | 03 | 0.00 | 0.00 | 0.00 | 0.00 | 0.00 | 0.00 | 0.00 | 0.00 | 0.00 | | | |
| 0 | 03 | 55.00 | 12.43 | 7.64 | 21.50 | 39.01 | 45.72 | 89.69 | 0.00 | 0.00 | | | |
| 0.5 | 04 | 3.00 | 0.00 | 0.00 | 0.00 | 0.00 | 0.00 | 0.00 | 0.00 | 0.00 | | | |
| 0 | 04 | 77.00 | 50.07 | 0.00 | 2.19 | 28.38 | 26.69 | 58.60 | 26.74 | 0.00 | | | |
| 0.5 | 05 | 1.00 | 0.00 | 0.00 | 0.00 | 0.00 | 0.00 | 0.00 | 0.00 | 0.00 | | | |
| 0 | 05 | 57.00 | 19.52 | 2.36 | 25.90 | 0.00 | 62.85 | 6.04 | 18.72 | 8.66 | | | |
| 0.5 | 06 | 1.00 | 0.00 | 0.00 | 0.00 | 0.00 | 0.00 | 0.00 | 0.00 | 0.00 | | | |
| 0 | 06 | 69.00 | 0.00 | 0.00 | 13.32 | 15.69 | 39.08 | 1.01 | 20.95 | 0.00 | | | |
| 0 | 07 | 54.00 | 29.779 | 0.00 | 31.79 | 35.24 | 85.55 | 45.62 | 0.00 | 71.82 | | | |
| 0.5 | 07 | 1.00 | 0.00 | 0.00 | 0.00 | 0.00 | 0.00 | 0.00 | 0.00 | 0.00 | | | |
| 0.50 | 08 | 2.00 | 0.00 | 0.00 | 0.00 | 0.00 | 0.00 | 0.00 | 0.00 | 0.00 | | | |
| 0 | 08 | 60.00 | 0.00 | 31.20 | 22.70 | 45.84 | 14.74 | 13.37 | 0.00 | 24.45 | | | |

These data indicate that a huperzine compound such as huperzine A reliably reduced pain. The acute phase of the model is relevant to non-neuropathic pain such as that associated with injury and inflammation, and the inflammatory phase of the model is relevant to neuropathic pain.

Reduction in Seizure Disorders

Two to 4 million Americans suffer from recurrent seizures. Methods of diagnosing individuals suffering from or at risk of developing a seizure disorder are well known in the art (Saunders Manual of Neurologic Practice, R. Evans, ed. p. 244-255; Office Practice of Neurology, $2^{nd}$ edition, Samuels et al., eds. Churchill, Livingston Press, p. 928-937).

The huperzine compounds described herein are useful to treat a diverse range of seizures or preventing epilepsy and the onset of seizures (epileptogenesis). Seizures are typically divided into generalized seizures (absence, atonic, tonic-clonic, myoclonic) and partial (simple and complex) seizures.

A significant advantage of huperzine compounds compared to other drugs used for epilepsy is that huperzine compounds not only prevent and reduce the frequency/severity/duration of epileptic seizures, these compounds also have the added benefit of neuroprotection by virtue of their interaction with acetylcholinesterase. Epilepsy, particularly temporal lobe epilepsy, can be associated with progressive memory deterioration (by a mechanism unrelated to AD) and becomes more severe with ongoing seizures. Huperzine compounds reduce or slow the progression of epilepsy-associated memory loss.

(a) Generalized Seizures

Generalized seizures affect both cerebral hemispheres (sides of the brain) from the beginning of the seizure. They produce loss of consciousness, either briefly or for a longer period of time, and are sub-categorized into several major types: generalized tonic clonic; myoclonic; absence; and atonic.

Absence seizures (also called petit mal seizures) are lapses of awareness, sometimes with staring, that begin and end abruptly, lasting only a few seconds. There is no warning and no after-effect. Some absence seizures are accompanied by brief myoclonic jerking of the eyelids or facial muscles, or by variable loss of muscle tone. More prolonged attacks may be accompanied by automatisms, which may lead them to be confused with complex partial seizures. However, complex partial seizures last longer, may be preceded by an aura, and are usually marked by some type of confusion following the seizure.

Myoclonic seizures are rapid, brief contractions of bodily muscles, which usually occur at the same time on both sides of the body. Occasionally, they involve one arm or a foot. People usually think of them as sudden jerks or clumsiness. A variant of the experience, common to many people who do not have epilepsy, is the sudden jerk of a foot or limb during sleep.

Atonic seizures produce an abrupt loss of muscle tone. Other names for this type of seizure include drop attacks, astatic or akinetic seizures. They produce head drops, loss of posture, or sudden collapse. Because they are so abrupt, without any warning, and because the people who experience them fall with force, atonic seizures can result in injuries, such as to the head and face.

Generalized tonic clonic seizures (grand mal seizures) are the most common and best known type of generalized seizure. They begin with stiffening of the limbs (the tonic phase), followed by jerking of the limbs and face (the clonic phase). During the tonic phase, breathing may decrease or cease altogether, producing cyanosis (blueing) of the lips, nail beds, and face. Breathing typically returns during the clonic (jerking) phase, but it may be irregular. This clonic phase usually lasts less than a minute. Some people experience only the tonic, or stiffening phase of the seizure; others exhibit only the clonic or jerking movements; still others may have a tonic-clonic-tonic pattern.

(b) Partial Seizures

In partial seizures the onset of the electrical disturbance is limited to a specific area of one cerebral hemisphere (side of the brain). Partial seizures are subdivided into simple partial seizures (in which consciousness is retained); and complex partial seizures (in which consciousness is impaired or lost). Partial seizures may spread to cause a generalized seizure, in which case the classification category is partial seizures secondarily generalized.

Partial seizures are the most common type of seizure experienced by people with epilepsy. Virtually any movement, sensory, or emotional symptom can occur as part of a partial seizure, including complex visual or auditory hallucinations. There are two types of partial seizure, simple partial seizures and complex partial seizures.

Complex partial seizures generally affect a larger area of the brain than simple partial seizures and they affect consciousness. During a complex partial seizure, a person cannot interact typically normally with other people, is not in control of his movements, speech, or actions; doesn't know what he's doing; and cannot remember afterwards what happened during the seizure. Although someone may appear to be conscious because he stays on his feet, his eyes are open and he can move about, it will be an altered consciousness, a dreamlike, almost trancelike state. A person may even be able to speak, but the words are unlikely to make sense and he or she will not be able to respond to others in an appropriate way. Although complex partial seizures can affect any area of the brain, they often affect one or both of the brain's two temporal lobes. Because of this, the condition is sometimes called "temporal lobe epilepsy."

(c) Epilepsy

Epileptic seizures are the outward manifestation of excessive and/or hypersynchronous abnormal activity of neurons in the cerebral cortex. Many types of seizures occur, as described above. The neuromechanism responsible for seizures includes the amygdala, the hippocampus, the hypothalamus, the parolfactory cortex, the frontal and temporal lobes, and the involvement of the substantia nigra, a particular portion of the brain considered to be part of neural circuitry referred to as the basal ganglia.

The methods and compositions of the invention are to be used to inhibit, reduce, or treat seizures that include, but are not limited to, tonic seizures, tonic-clonic seizures, atypical absence seizures, atonic seizures, myoclonic seizures, clonic seizures, simple partial seizures, complex partial seizures, and secondary generalized seizures.

Various in vivo models of seizures and epilepsy that are used to test huperzine against specific forms of seizures and epilepsy, e.g., Maximal Electroshock (MES) model and Subcutaneous Metrazole (SCMET) model. For example, the kainate model is an epileptic model in which kainic acid, one of the excitatory amino acids found in the brain, is injected to nuclei (amygdala, hippocampus, etc.) in the limbic system in a microamount to induce focal epilepsy. The kainate model serves as a model for an epileptic seizure; more particularly, as a model for status epilepticus induced from the limbic system in an acute phase, and as a model for evolution of a spontaneous limbic seizure to a secondary generalized seizure in a chronic phase. The kainate model may also be used as a cortex epilepsy model through injection of kainic acid to the cortex (sensory motor field). For a review of animal models used for epilepsy and seizures, see for example, Sarkisian (2001) *Epilepsy and Behavior,* 2: 201-216).

To investigate the neurotoxicity levels of the huperzine compounds, the Toxicity Model (TOX) using a rotorod is employed. The animals (e.g., mice) were trained to stand on an accelerating rotorod rotating at 10 rev $min^{-1}$ with a diameter of 3.2 cm. The trained animal can be given the huperzine compound at various doses and the effect of huperzine on their motor skills can be determined. The dose at which the animals fell off the rotorod is the toxic dose.

(d) Epileptogenesis

Epileptogenesis is the process by which a normal brain becomes chronically prone to seizures. Many brain insults (stroke, trauma, neurodegenerative disease etc) can induce epileptogenesis, yet no therapies exist to disrupt this process. Although reorganization of specific neuronal circuits and alterations in individual synapses are associated with epileptogenesis, the functional consequences and relative importance of these changes to epileptogenesis and seizure genesis are unknown, as are many of the molecular and cellular mechanisms underlying these alterations.

Seizures and epilepsy are common sequalae of acute brain insults such as stroke, traumatic brain injury, and central nervous system infections. Early, or acute symptomatic, seizures occur at the time of the brain insult and may be a marker of severity of injury. A cascade of morphologic and biologic changes in the injured area over months to years leads to hyperexcitability and epileptogenesis. After a variable latency period, late unprovoked seizures and epilepsy occur. The drugs that presently used in the treatment of epilepsy, treat the symptom, seizures, but do not modify the epileptogenic process.

Huperzine is administered during the latent period for the prevention of epileptogenesis and the development of unprovoked seizures and epilepsy, and huperzine is used as a neuroprotectant and an antiepileptogenic agent.

Models that can be used to test the neuroprotectant and an anti-epileptogenic effects of therapeutic agents include a kindling model (Wada, (1974) *Epilepsia* 19: 217-227; Sato et al., (1990) *Epilepsy Research* 5: 117-124); Silver et al., (1991) *Ann. Neurol.* 29: 356-363). Seizure kindling models are characterized by giving a sub-seizure eliciting electrical or chemical stimulus (i.e., sub-threshold) over a period of time (Goddard et al., (1969) *Exp. Neurol.* 25: 295-330). The majority of initially non-convulsive animals that are exposed to such stimuli over a number of days, eventually exhibit seizure activity to these stimuli, have a permanently lowered seizure threshold, and exhibit altered manifestations of normal behavior and, therefore, are considered "kindled." The kindling phenomenon has been proposed to underlie the development of disorders such as certain types of epilepsy syndromes. Several kindling models of seizure development have been characterized. Huperzine compounds are useful to decrease the severity and duration of cerebral insults including, but not limited to, degeneration (e.g., degeneration that occurs in AD), ischemia, haemorrhagic stroke, trauma, and infection, that can lead to an elevated incidence of seizure disorders.

Experiments to evaluate the effect of huperzine A on seizure disorders were carried out as follows. Huperzine A was evaluated in the Maximal Electroshock (MES) and Subcutaneous Metrazol (pentylenetetrazol; SCMET) models of generalized tonic-clonic and myoclonic seizures, respectively in mice and rats.

The maximal electroshock (MES) model is an art recognized test, useful to investigate the efficacy of therapeutic agents against grand mal seizures. Maximal seizures were induced by the application of electrical current to the brain via corneal electrodes. The stimulus parameters for mice were 50 mA in a pulse of 60 Hz for 200 ms. The animals were given the huperzine dissolved in methyl cellulose and spasm inhibition was recorded as a measure of anticonvulsant activity.

The Subcutaneous Metrazole (SCMET) model is also an art-recognized test for therapeutic agents for epilepsy, and in particular, is useful for investigating petite mal seizures. A Metrazole dose of 85 mg/kg was administered subcutaneously to induce seizures. Huperzine was then administered and the animals observed.

The neurotoxicity of huperzine was tested in the rotorod test. The mice were trained to stand on an accelerating rotorod rotating at 10 rev min$^{-1}$ with a diameter of 3.2 cm. The trained animals were given the huperzine at various doses and the effect of huperzine on their motor skills was determined. The dose at which the animals fell off the rotorod was the toxic dose.

Huperzine A was either administered in a soluble form (SOL) or as a suspension (SUS). At concentrations of 0.1-0.3 mg/kg, huperzine A was readily soluble in the methyl cellulose solvent. However, at higher concentrations, the huperzine A was not soluble and was therefore administered to the animal as a suspension. To produce the suspension, huperzine A was ground to a powder using a mortar and pestle, and the powder mixed with methyl cellulose. This mixture was then sonicated to produce a suspension that was subsequently administered to mice in the weight range of 19.0 to 25.5 g. Two time points were analyzed at each concentration of huperzine A with each animal model and the results shown in Table 1. The data are presented as the number of mice showing an effect (N) from the full number of mice (F) tested. For example, huperzine A at a concentration of 3 mg/kg in the MES model, results in one mouse being protected against seizures (N) out of a total three mice that were tested (F), at 30 minutes post administration (i.e., 33% were protected). At four hours post administration, all three mice were protected (i.e., 100% were protected). This indicates that the huperzine A is reactive by 30 minutes and is fully reactive by 4 hours.

TABLE 6

Results of the effect of Huperzine A in Mice I.P. Identification

| Test | Dose (mg/kg) | Form | Time (Hours) 0.5 N/F | 4.0 N/F |
|---|---|---|---|---|
| MES | 0.1 | SOL | / | 0/4 |
| MES | 0.3 | SOL | / | 0/4 |
| MES | 1 | SUS | 0/1 | 1/1 |
| MES | 3 | SUS | 1/3 | 3/3 |
| MES | 10 | SUS | 1/1 | 1/1 |
| SCMET | 1 | SOL | 3/5 (MJ)[1] | 0/1 |
| SCMET | 3 | SUS | 1/1 (MJ) | 0/1 |
| SCMET | 10 | SUS | 0/1 | 1/1 (MJ) |
| TOX | 0.1 | SOL | / | 0/4 |
| TOX | 0.3 | SOL | / | 0/4 |
| TOX | 1 | SOL | 4/4 (T)[2] | 2/2 (T) |

TABLE 6-continued

Results of the effect of Huperzine A in Mice I.P. Identification

| Test | Dose (mg/kg) | Form | Time (Hours) 0.5 N/F | 4.0 N/F |
|---|---|---|---|---|
| TOX | 3 | SUS | 8/8 | 4/4 (T) |
| TOX | 10 | SUS | 4/4 | 2/2 (T) |
| TOX | 30 | SUS | 4/4 (D)[3] | / |
| TOX | 100 | SUS | 8/8 (D) | / |
| TOX | 300 | SUS | 4/4 (D) | / |

[1](MJ) Animals displaying myoclonic jerks.
[2](T) Animals displaying tremors.
[3](D) Death of animals.

A similar experiment was conducted to determine the time course of huperzine A in mice following I. P. administration of huperzine A. The huperzine A was prepared as described above and a 5 mg/kg dose concentration was administered to mice in the weight range of 105 to 135 g. The effects of a 5 mg/kg dose of huperzine A was tested in the MES and TOX animal models. The results are summarized in Table 7 and show that a dosage of 5 mg/kg huperzine A was toxic in all animals within 30 minutes post administration. The toxicity in mice is attributed to the effect of huperzine A on acetylcholinesterase. This toxicity profile is generally not observed in humans. Thus, a higher relative dose of a huperzine compound is tolerated in humans compared to rodents.

TABLE 7

Time Course Study of Huperzine A in Mice

| Test Dose (mg/kg) | Time (Hours) | | | | | |
|---|---|---|---|---|---|---|
| | 0.25 N/F | 0.5 N/F | 1.0 N/F | 2.0 N/F | 4.0 N/F | 6.0 N/F |
| MES 5 | / | 1/4 | 3/4 | 3/4 | 3/4 | 4/4 |
| TOX 5 | / | 4/4 | 4/4 (ST)[4] | 4/4 (ST) | 4/4 | 4/4 (ST) |

[4](ST) Animals displaying severe tremors.

A similar experiment was conducted to determine the time-course of huperzine A in rats following oral administration. The huperzine A was prepared in the same way as described above and a dose of 1 mg/kg was orally administered to rats with a weight in the range of 120 to 155 g. The effects of a 1 mg/kg dose of huperzine A was tested in each of the models and the results summarized in Table 8. The data show that there was no toxicity in any of the animals treated with a dose of 1 mg/kg of huperzine A. The results also suggest that the peak activity of huperzine A occurs between 30 minutes and two hours post administration.

TABLE 8

Time Course Study of Huperzine A in Rats

| Test Dose (mg/kg) | Time (Hours) | | | | | |
|---|---|---|---|---|---|---|
| | 0.25 N/F | 0.5 N/F | 1.0 N/F | 2.0 N/F | 4.0 N/F | 6.0 N/F |
| MES 1 | 0/4 | 0/4 | 1/4 | 1/4 | 0/4 | 0/4 |
| SCMET 1 | 0/4 | 2/4 | 2/4 | 1/4 | 1/4 | 0/4 |
| TOX 1 | 0/4 | 0/4 | 0/4 | 0/4 | 0/4 | 0/4 |

Peak anticonvulsant activity was observed one-hour after p.o. administration of 1 mg/kg. At the doses tested (i.e., 1, 2, and 4 mg/kg), a maximum of 62.5% protection was observed at a non-toxic dose of 1 mg/kg. Behavioral motor impairment in 75% and 100% of mice tested was observed at doses of 2 and 4 mg/kg, respectively.

These results demonstrated that huperzine A is orally bioavailable and reaches effective brain concentrations. The data also support the use of huperzine A in neuroprotective therapy for the prevention of epileptogenesis and seizure-induced neuronal toxicity.

HupA was also evaluated for its ability to modify tonic extension, minimal clonic, limbic seizures in the maximal electroshock seizure (MES), subcutaneous pentylenetetrazol (sc PTZ), and 6 Hz seizure tests following intraperitoneal administration. These three tests are highly predictive of efficacy against human generalized tonic-clonic (MES), generalized myoclonic (sc PTZ), and refractory limbic (6 Hz) seizures, respectively. In addition, it was tested for its ability to prevent the expression of Stage V seizures in the hippocampal kindled rat model of partial epilepsy.

Male, 18-25 g CF1 mice and 100-125 g Sprague-Dawley rats (Charles River Laboratories, Wilmington, Mass.) were used as the experimental animals. Animals were pretreated intraperitoneally (i.p.) with increasing doses of HupA and tested at various times after administration for protection against tonic extension (MES test), minimal clonic (s.c. PTZ test), limbic (6 Hz), or secondarily generalized (kindled rat) seizures. Seizure testing was carried out as follows. For the MES and 6 Hz tests, a drop of anesthetic/electrolyte solution (0.5% tetracaine hydrochloride in 0.9% saline) was applied to the eyes of each animal prior to placement of the corneal electrodes. The electrical stimulus in the MES test was 50 mA, 60 Hz, for mice and 150 mA, 60 Hz, for rats, delivered for 0.2 sec (White et al., 2002, In R. H. Levy et al., eds. Antiepileptic Drugs, 5$^{th}$ edition, p. 36-48, Philadelphia: Lippincott Williams & Wilkins). The ability of the test substance to prevent seizures induced by 6 Hz corneal stimulation (32 mA, 3 sec duration) was assessed at various times after i.p. administration of 1 mg/kg HupA For assessment of hippocampal kindling, HupA (1 mg/kg, i.p.) was administered. The ability of the compound to block the expression of hippocampal kindled seizures was evaluated using the rapid hippocampal kindling model (White et al., 2002). Animals not displaying secondarily generalize seizures were considered protected.

Minimal toxicity was identified in mice by the rotorod procedure. In rats, minimal motor impairment (MMI) was determined by overt evidence of ataxia, abnormal gait and stance. Quantitation: Where appropriate, the median convulsive current (CC50) required to produce the desired endpoint in 50% of animals tested and 95% confidence intervals were then calculated by Probit analysis (Finney, D. J., 1971, Probit Analysis, 3$^{rd}$ ed., London, Cambridge University Press).

Figure 2:
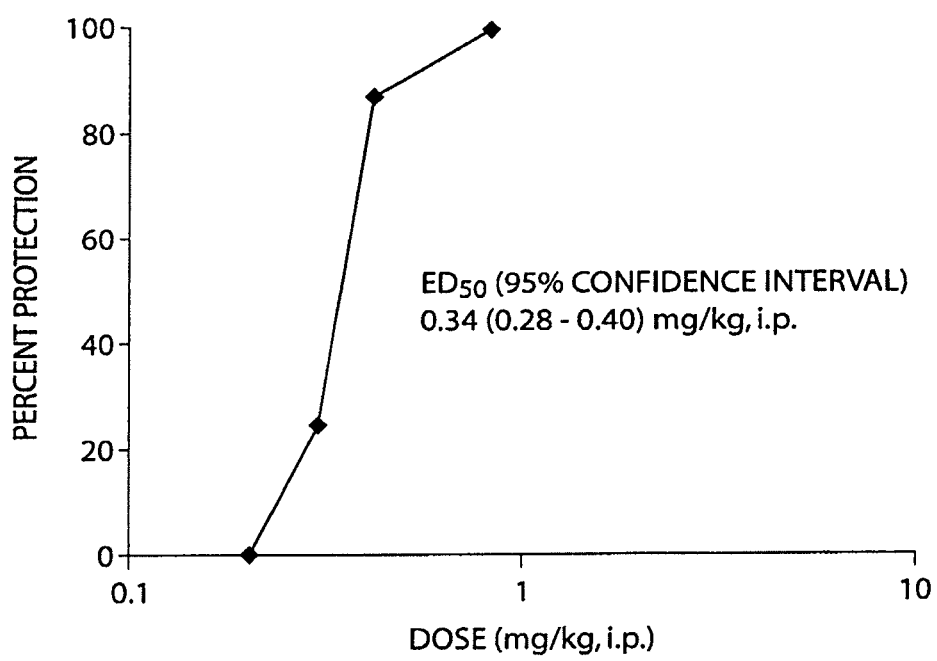
FIG. 2 is a line graph showing that Huperzine A displays dose-dependent protection against 6 Hz seizures.
Figure 3:
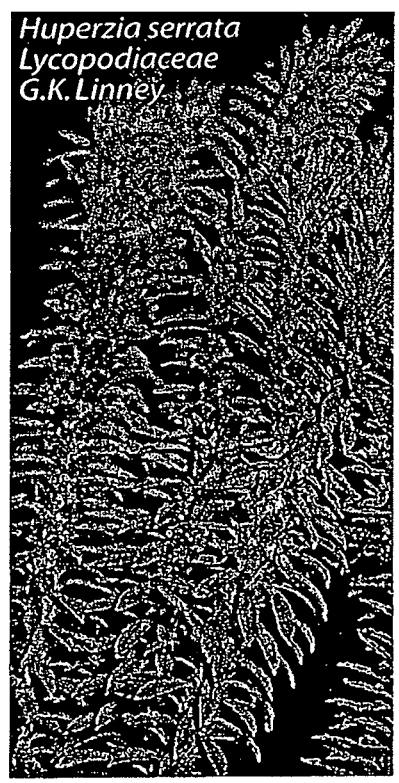
FIG. 3 is a photograph of *Huperzia serrata* Lycopodiaceae, a botanical source of Huperzine A.

The results of the study are shown in FIGS. 1, 2 and Table 9. Regarding behavioral impairment, HupA was found to produce marked motor impairment in both mice and rats at anticonvulsant doses. Marked tremor activity was also observed at anticonvulsant doses, presumably related to its inhibition of acetyl-cholinesterase.

TABLE 9

Summary of Anticonvulsant Activity Of HupA in Rats and Mice

| Test | Species | Dose (mg/kg), route | Time of test (h) | Maximum Protection Observed |
|---|---|---|---|---|
| scPTZ | Rat | 2 mg/kg, p.o. | ½ | 62.5% |
| Hippocampal Kindling | Rat | 1 mg/kg, i.p. | ¼-3 | 0% |
| MES | Mouse | 1 mg/kg, i.p. | 1 & 2 | 75% |
| scPTZ | Mouse | 1 mg/kg, i.p. | 2 | 25% |
| 6 Hz | Mouse | 0.83 mg/kg, i.p. | 1 | 100% |

When injected into mice, the alkaloid HupA produced a potent, time-dependent, anticonvulsant effect against generalized and pharmaco-resistant limbic seizures. These data regarding HupA's effect in the 6 Hz psychomotor seizure model indicate that this molecule offers a significant advantage over the established antiepileptic drugs phenyloin, carbamazepine, lamotrigine, and topiramate, all of which display limited efficacy in this model. These effects were observed at doses that produced marked behavioral toxicity in both mice and rats which was characterized by tremor, ataxia, and rotarod impairment. However, similar toxicity has not been observed in patients treated with HupA In published clinical studies of HupA conducted in patients, adverse effects were noted infrequently and were mainly cholinergic, including dizziness, nausea, gastrointestinal symptoms, sweating and depressed heart rate. The results indicate that the unique profile of HupA in the 6 Hz limbic seizure model and its action as an NMDA receptor antagonist is useful for the prevention and treatment of refractory partial epilepsy.

Quantitative data was obtained for Huperzine A in a 6 Hz model as described above (Barton et al., 2001, Epilepsy Res. 47:217-227) using three levels of electrical stimulation. When animals were dosed via i.p. injection, the $ED_{50}$ values were 0.28, 0.34, and 0.78 mg/kg for 22, 32, and 44 mA, respectively. Some minimal motor impairment in some animals even at low doses, the $ED_{50}$ values for 22 and 32 mA were still below the $TD_{50}$ of 0.83 mg/kg.

TABLE 10

Anticonvulsant Evaluation (6 Hz, Mice)

| Add ID: | 357133A | Screen ID: 1 | | | |
|---|---|---|---|---|---|
| Solvent Code: | MC | Solvent Prep: | M&P, SB | Route Code: IP | Current (mA): 22 |
| Animal Weight: | to | g | | | |

TABLE 11

ED50 Values

| Test | Time (Hrs) | ED50 | 95% Confidence Interval LOW | 95% Confidence Interval HIGH | SLOPE | STD. ERR. | PI VALUE |
|---|---|---|---|---|---|---|---|
| 6 HZ | 1 | 0.279 | 0.163 | 0.483 | 2.69 | 0.849 | |

TABLE 12

ED50 Biological Response

| Test | Dose (mg/kg) | Dths | N/F | C |
|---|---|---|---|---|
| 6 HZ | 0.09 | | 1/8 | |
| 6 HZ | 0.175 | | 2/8 | 15 |
| 6 HZ | 0.35 | | 5/8 | 15 |
| 6 HZ | 0.7 | | 7/8 | * |

| TEST | DOSE (mg/kg) | TIME | CODE | COMMENT |
|---|---|---|---|---|
| 6 HZ | 0.18 | 1 | 15 | Minimal motor impairment |

-continued

| TEST | DOSE (mg/kg) | TIME | CODE | COMMENT |
|---|---|---|---|---|
| 6 HZ | 0.35 | 1 | 15 | Minimal motor impairment |
| 6 HZ | 0.7 | 1 | 33 | Tremors |
| 6 HZ | 0.7 | 1 | 15 | Minimal motor impairment |

TABLE 13

Anticonvulsant Evaluation (6 Hz, Mice)

| Add ID: | 357133A | Screen ID: 1 | | | |
|---|---|---|---|---|---|
| Solvent Code: | MC | Solvent Prep: | M&P | Route Code: IP | Current (mA): 32 |
| Animal Weight: | to | g | | | |

TABLE 14

ED50 Values

| | Time | | 95% Confidence Interval | | | | PI |
|---|---|---|---|---|---|---|---|
| Test | (Hrs) | ED50 | LOW | HIGH | SLOPE | STD. ERR. | VALUE |
| 6 HZ | 1 | 0.339 | 0.28 | 0.404 | 13.17 | | 4.91 |

TABLE 15

ED50 Biological Response

| Test | Dose (mg/kg) | Dths | N/F | C |
|---|---|---|---|---|
| 6 HZ | 0.2 | | 0/8 | 33 |
| 6 HZ | 0.3 | | 2/8 | * |
| 6 HZ | 0.415 | | 7/8 | * |
| 6 HZ | 0.83 | | 8/8 | * |

| TEST | DOSE (mg/kg) | TIME | CODE | COMMENT |
|---|---|---|---|---|
| 6 HZ | 0.2 | 1 | 33 | Tremors |
| 6 HZ | 0.3 | 1 | 33 | Tremors |
| 6 HZ | 0.3 | 1 | 15 | Minimal motor impairment |
| 6 HZ | 0.42 | 1 | 33 | Tremors |
| 6 HZ | 0.42 | 1 | 15 | Minimal motor impairment |
| 6 HZ | 0.83 | 1 | 33 | Tremors |
| 6 HZ | 0.83 | 1 | 15 | Minimal motor impairment |

TABLE 16

Time to Peak Effect

| | | # Dths | | | | | | | | | | | | | | | | | |
|---|---|---|---|---|---|---|---|---|---|---|---|---|---|---|---|---|---|---|---|
| | | 0.25 | | 0.5 | | 1.0 | | 2.0 | | 4.0 | | 6.0 | | 8.0 | | 24 | | 3.0 | |
| Test | Dos (mg/kg) | N/F | C | N/F | C | N/F | C | N/F | C | N/F | C | N/F | C | N/F | C | N/F | C | N/F | C |
| 6 HZ | 0.83 | 1/4 | * | 1/4 | * | 4/4 | * | 2/4 | * | 0/4 | 15 | / | | / | | / | | / | |

Huperzine

Hup A, a sesquiterpene alkaloid derived from Chinese club moss (*Huperzia serrata*). A huperzine compound is one that conforms to the structure of Formula I. The term huperzine as used herein includes huperzine A and huperzine B, analogs of huperzine A and huperzine B, derivatives of huperzine A and huperzine B and salts and hydrates thereof. The term huperzine also encompasses all homologs, positional isomers, and all stereoisomers and mixtures of stereoisomers in optically active or racemic form of huperzine A and huperzine B and salts and hydrates thereof. Huperzine is a small molecule and is readily able to penetrate the blood-brain barrier and enter into the central nervous system of the subject. An analogue refers to a chemical compound that is structurally similar to a parent compound and has chemical properties or pharmaceutical activity in common with the parent compound.

The following terms relate to Formula I and identification of substituents relative to the structure/formula.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. In certain compounds, a straight chain or branched chain alkyl has six or fewer carbon atoms in its backbone (e.g., $C_1$-$C_6$ for straight chain, $C_3$-$C_6$ for branched chain). In some examples, a straight chain or branched chain alkyl has four or fewer carbon atoms in its backbone. Further, cycloalkyls have from three to eight carbon atoms in their ring structure. For example, cycloalkyls have five or six carbons in the ring structure. "$C_1$-$C_6$" includes alkyl groups containing one to six carbon atoms.

The term "substituted alkyl" refers to alkyl moieties having substituents replacing a hydrogen on at least one carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Substituted Alkyl"

further includes alkyl groups that have oxygen, nitrogen, sulfur or phosphorous atoms replacing at least one hydrocarbon backbone carbon atoms.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at least one ring position with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl). In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and, for example, have five or six carbons in the ring structure. The term "$C_2$-$C_6$" includes alkenyl groups containing two to six carbon atoms. The term "substituted alkenyl", refers to alkenyl moieties having substituents replacing a hydrogen on at least one hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. The term "substituted alkenyl" further includes alkenyl groups which include oxygen, nitrogen, sulfur or phosphorous atoms replacing at least one hydrocarbon backbone carbons.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "substituted alkynyl" refers to alkynyl moieties having substituents replacing a hydrogen on at least one hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. The term "substituted alkynyl" further includes alkynyl groups having oxygen, nitrogen, sulfur or phosphorous atoms replacing at least one hydrocarbon backbone carbons.

Unless the number of carbons is otherwise specified, "lower alkyl" includes an alkyl group, as defined above, but having from one to eight, for example, from one to six, carbon atoms in its backbone structure. "Lower alkenyl" and "lower alkynyl" have chain lengths of, for example, 2-8 carbon atoms.

"Alkoxyalkyl", "alkylaminoalkyl" and "thioalkoxyalkyl" include alkyl groups, as described above, which further include oxygen, nitrogen or sulfur atoms replacing at least one hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl", or "heterocyclic group" include closed ring structures, e.g., 3- to 10-, or 4- to 7-membered rings, which include at least one heteroatoms. The term "heteroalkyl" includes alkyl groups which contain at least one heteroatom. "Heteroatom" includes atoms of any element other than carbon or hydrogen. Examples of heteroatoms include nitrogen, oxygen, sulfur and phosphorus. The term "heteroalkyl" includes cycloalkyl groups e.g., morpholine, piperidine, piperazine, etc.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at least one positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at least one constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —$O^-$.

The term "halogen" includes fluorine, bromine, chlorine, iodine, etc. The term "perhalogenated" generally refers to a moiety wherein all hydrogens are replaced by halogen atoms.

The structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

The structure of some of the compounds of the invention include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this invention may exist in stereoisomeric form, therefore can be produced as individual stereoisomers or as mixtures.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Calm et al, Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Calm, J. Chem. Educ. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, huperzine compounds, e.g., the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that compounds of Formula I may be depicted as different tautomers. When compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by formula I are indole derivatives, and have formula I as a common core.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

References to pharmaceutically acceptable salts include solvent addition forms (solvates) or crystal forms (polymorphs) as defined herein, of the same salt. The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxylamine-containing, and imine-containing compounds of the present invention.

Huperzine A, an alkaloid, has been isolated from the Chinese moss *Huperzia serrata* (U.S. Pat. No. 5,177,082 to Yu et al.; Liu et al. (1986) *Can. J. Chem.* 64:837; Ayer et al. (1989) *Can. J. Chem.* 67:1077; Ayer et al. (1989) *Can. J. Chem.* 67:1548). Huperzine A is an acetylcholinesterase inhibitor, and Huperzine B, also derived from *Huperzia serrata*, is a much less potent acetylcholinesterase inhibitor.

The structures of huperzine A and huperzine B are shown in J. Liu et al. (1986) *Can. J. Chem.* 64:837-839, incorporated herein by reference. Natural huperzine A is a chiral molecule also called L-huperzine A or (−)-huperzine A. The prefix (−) is typically used to describe so-called "left-handed" natural chiral huperzine compositions. However, Huperzine can also be synthesred as a right-handed (+) molecule or as a racemic mixture (+). Huperzine A is also known as HUP, hup A and selagine. Huperzine A may also be an NMDA receptor antagonist as indicated in the examples section. The structures of (−)-huperzine A and (−)-huperzine B are also depicted below.

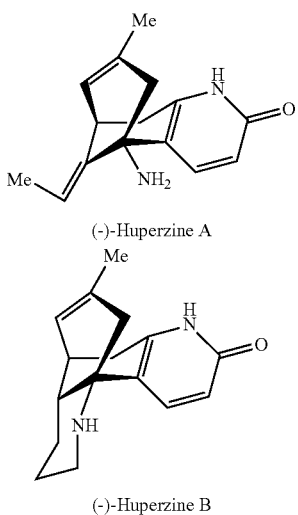

(-)-Huperzine A (-)-Huperzine B

The invention also pertains to using analogs and derivatives of huperzine. In one embodiment, the analogs and derivatives of huperzine differentiate the AChE inhibition properties of huperzine from the NMDA receptor antagonist properties of huperzine. The analogs and derivatives of huperzine A or huperzine B, respectively, have the generic chemical structures A and B below:

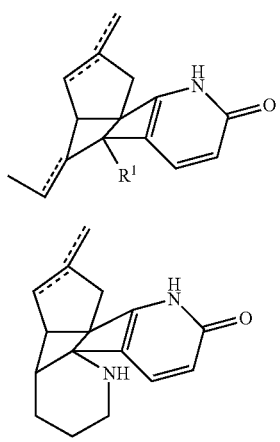

where $R^1$ represents $NH_2$ or a suitable substituent as defined below and the dotted line represents the optional presence of a carbon-carbon bond that, when present, completes a carbon-carbon double bond. In one embodiment, an analog or derivative of huperzine A or huperzine B will have preventative and/or neuroprotective activity when tested as set forth in examples described below. In another embodiment, the analog or derivative of hyperzine A or huperzine B will have seizure alleviating activity. In another embodiment, the analog or derivative of hyperzine A or huperzine B will have a hypotension alleviating activity. In another embodiment, analogs or derivatives of huperzine A or huperzine B will have pain alleviating activity. In another embodiment, the analogs or derivatives of huperzine A or huperzine B are designed to reduce side effects of huperzine. One of skill in the art can readily identify analogs and derivatives of huperzine suitable for use with invention by obtaining compounds with core structures A and B and testing those compounds for neuroprotective activity as set forth in the examples below.

Huperzine A and huperzine B can act through different receptors, or bind to different regions of the same receptor. The combination of both huperzine A and huperzine B may also mean that lower dosages of huperzine A and huperzine B can be used to achieve the same therapeutic effect as huperzine A, or huperzine B used alone. This is important when a desired therapeutic effect occurs at a high dose of huperzine, e.g., huperzine A, but which also leads to adverse side effects. In such an instance, a lower dosage of huperzine A can be combined with a dosage of huperzine B to provide the desired therapeutic effect, but without the adverse side effects.

Examples of huperzine A compounds include, but are not limited to, the huperzine analogs in U.S. Pat. No. 4,929,731; U.S. Pat. No. 5,106,979; U.S. Pat. No. 5,663,344; and U.S. Pat. No. 5,869,672; dihydro-desmethyl-huperzine, 11-desmethyl-11-chloro-huperzine A, and the compounds of U.S. Pat. No. 5,104,880; the compounds of U.S. Pat. No. 5,177,082; the huperzine derivatives of U.S. Pat. No. 5,929,084; and the huperzine analogs of U.S. Pat. No. 5,547,960, all of which patents are hereby incorporated herein by reference. Examples of huperzine B compounds and its analogs can readily be synthesized using standard chemistry (Ma et al. (1998) *Ann NY Acad Sci.* 854:506-7; Ma et al. (1998) *N-S Arch Pharmacol* 358:suppl 1, P53194; Jiang H et al. (2003) *Medicinal chemistry* 10:2231-2252; Rajendran et al. (2002) *Bioorg. Med. Chem. Lett.* 12:1521-1523; Wang et al. (1999) *Neuroscience Letters* 272:21-24; and Yan et al. (1987). *Acta Pharmacol. Sin* 8: 117).

Preferred among these various huperzine compounds are huperzine A and huperzine B, including (−)-huperzine A, (+)-huperzine A, (+)-huperzine A, (−)-huperzine B, (+)-huperzine B, and (+)-huperzine B.

The Glutamate Neurotransmitter System and NMDA Subtypes of Glutamate Receptors

A huperzine compound is used as an NMDA receptor antagonist in a disorder associated with the NMDA receptor function, e.g., seizures, epilepsy, epileptogenesis, and neuropathic pain. Glutamate is recognized as the predominant excitatory neurotransmitter (messenger molecule) in the mammalian central nervous system (CNS); for a review, see the chapter by Olney entitled "Glutamate" in The Encyclopedia of Neuroscience, edited by Adelman (either the 1987 or the 1995 edition). Glutamate is involved in excitatory transmitting messages from one nerve cell (neuron) to another in many different circuits within the CNS, and therefore serves many important functions.

There are several different subtypes of receptors through which glutamate transmits messages. A particularly important receptor through which glutamate mediates a wide range of functions is the N-methyl-D-aspartate (NMDA) receptor. Other major classes of glutamate receptors are kainic acid receptors and Quis/AMPA receptors; these two classes are collectively referred to as non-NMDA receptors. Both NMDA and non-NMDA receptors are normally activated by glutamate.

Antagonist drugs that block glutamate receptors, such as the NMDA receptor, are classified in two broad classes of compounds. One class is referred to as competitive NMDA antagonists; these agents bind at the NMDA/glutamate binding site (such drugs include CPP, DCPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Another class is referred to as non-competitive NMDA antagonists; these agents bind at other sites in the NMDA receptor complex (such drugs include phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715).

Huperzine A is used as an NMDA receptor antagonist to ameliorate, reduce or treat the effects of a disorder associated with the NMDA receptor. In another embodiment, the invention pertains to using huperzine B as an NMDA receptor antagonist. In yet another embodiment, the invention pertains to using a combination of huperzine A and huperzine B as an NMDA receptor antagonist.

Acetylcholinesterase (AChE) Inhibitors

A huperzine compound is also used as an acetylcholinesterase (AChE) inhibitor in disorders associated with aberrant acetylcholine (ACh) levels, such as orthostatic hypotension. AChE inhibitors limit the activity of the enzyme, acetylcholinesterase, which hydrolyzes the endogenous neurotransmitter ACh; and as such, AChE inhibitors preserve existing ACh levels in treated patients, and the resulting increase in extracellular ACh within the CNS reportedly restores central cholinergic hypofunction to a level that improves the disorder. There are several examples of AChE inhibitors that are commercially available (See, for example those AChE inhibitors set forth in Brufani et al, Alzheimer Disease: From Molecular Biology to Therapy, (1996) eds. Becker et al., 171-177; Schmidt et al., Alzheimer Disease: From Molecular Biology to Therapy, eds. Becker et al., 217-221 (1996); Vargas et al., Alzheimer Disease: From Molecular Biology to Therapy, eds. Becker et al. 251-255 (1996); Greig et al., Alzheimer Disease: From Molecular Biology to Therapy, eds. Becker et al, 231-237 (1996); and Giacobini, Alzheimer Disease: From Molecular Biology to Therapy eds. Becker et al. 187-204 (1996)).

Pain

Pain arises from excessive stimulation of NMDA receptors from presynaptic release of glutamate (Salter (2004) *J. Orofac Pain* 18: 318-24; and Ebert (1998) Biochem Pharmacol. 56: 553-9). Huperzine can be used as an antagonist of the NMDA receptor to reduce or prevent pain such as neuropathic pain.

A large number of disease states (e.g., cancer, AIDS), inflammatory conditions (e.g., arthritis), metabolic disorders (e.g., diabetes) and injuries (e.g., amputations) can give rise to chronic pain, pain persisting more than a few months; other forms of chronic pain have no known origin and are termed "idiopathic" pain. Neuropathic pain is pain occurring from dysfunction of the central or peripheral nervous system; it may also be a consequence of damage to peripheral nerves or to regions of the central nervous system, may result from disease or may be idiopathic. The common feature of each of these forms of pain is that a person may endure unrelenting pain that is usually resistant to common forms of analgesic therapy.

Symptoms of neuropathic pain include unusual sensations of burning, tingling, electricity, pins and needles, stiffness, numbness in the extremities, feelings of bodily distortion, allodynia (pain evoked by innocuous stimulation of the skin), and hyperpathia (an exaggerated pain response persisting long after the pain stimuli cease).

Several common causes of neuropathic pain are diabetes, cancer chemotherapy, herpes zoster infection, cervical or lumbar root compression owing to degenerative spine disease, malignant lesions of nerve plexus or root, nerve degeneration, such as from amputation, HIV infection, and lesions of central pain pathways, including spinothalamic tract, thalamus, or thalamic radiations. (Max (1991) Neuropathic Pain Syndromes, Advances in Pain Research and Therapy, 18).

Additional causes of neuropathic pain include drug-induced, or toxic, neuropathies. For example, anti-viral agents commonly cause peripheral neuropathies, as do phenyloin (a seizure medication), isoniazid (a tuberculosis medication), vincristine (a cancer chemotherapeutic agent), high dose vitamins, and folic acid antagonists.

Commonly used analgesics, such as morphine, codeine, tramadol, and aspirin only provide temporary relief from neuropathic pain. However, the analgesic effects of these compounds are almost always transient, and a majority of patients treated with these analgesics, still continue to experience pain. Thus, neuropathic pain is difficult to treat chronically with analgesics.

Huperzine A is useful as an NMDA receptor antagonist to ameliorate, reduce, prevent or treat the effects of a disorder associated with NMDA receptor function that results in neuropathic pain. Huperzine B is also useful as an NMDA receptor antagonist as is a combination of both compounds.

Orthostatic Hypotension

Huperzine A, B, a combination or analogues thereof are also used to prevent or treat orthostatic hypotension such as orthostatic hypotension that accompanies migraine headaches. Huperzine compounds have an added advantage compared to other drugs using for migraine headaches in that not only do the compound relieve pain associated with headache but also prevent or reduce the occurrence of episodes or orthostatic hypotension. Orthostatic hypotension is defined as a fall in blood pressure of at least 20 mm Hg systolic or 10 mm Hg diastolic within three minutes in the upright position. It is characterized by dizziness, light-headedness, visual blurring, and fainting when a person assumes a standing position. Orthostatic hypotension can be caused by various diseases and is classified as (i) "Central type" arising due to disorders such as Shy-Drager syndrome, intracranial tumor, Parkinsonism; (ii) "Peripheral type" arising due to disorders such as diabetes mellitus, angiitis, alcoholism, amyloidosis, acute pan-dysautonomia, familial dysautonomia (Riely-Day syndrome), syphilis (iii) "drug-induced orthostatic hypotension", and (iv) "idiopathic orthostatic hypotension". In most patients, orthostatic hypotension is of neurogenic origin, resulting from impaired cardiovascular adrenergic function.

Pharmaceutical Compositions

Huperzine A, B, are purified from natural sources using methods known in the art or synthesized according to known methods, e.g., Ward et al., 2006, Tetrahedron Letters 47:553-556). The huperzine compounds can be administered by virtually any mode and can be administered simultaneously or serially. When administered serially, the huperzine compounds should be administered sufficiently close in time so as to provide the desired effect, for example within 1-3 hours of each other. The huperzine compounds can be administered transdermally via a transdermal patch. For pain relief and/or administration for seizure disorders, one or more slow-release formulations are preferred compositions to optimize the pharmacokinetic properties. Slow release systems for an oral product include multiparticulate compositions such as Microtrol™ (Shire Labs) or OROS™ (Alza). Other sustained release systems include SODAS™ (Elan) as well as patch systems.

The huperzine compounds are administered therapeutically to treat, prevent, or slow the rate of onset of neuronal dysfunctions, such as epilepsy and seizures, or prophylactically to either protect against further seizures associated with epilepsy or to avoid or forestall the onset of seizures associated with other disorders. For example, the huperzine compositions can be administered prophylactically to slow or halt the progression of seizures and epilepsy in a patient who has had a stroke and has a risk of developing seizure as a result of the stroke. The huperzine compounds can also be administered to treat or prevent pain, such as neuropathic pain, and hypotension such as orthostatic hypotension.

The huperzine compounds can be administered to a subject, using a wide variety of routes or modes of administration. Suitable routes of administration include, but are not limited to, oral inhalation; nasal inhalation; transdermal; oral; rectal; transmucosal; intestinal; and parenteral administration, including intramuscular, subcutaneous, and intravenous injections. The huperzine compounds can be administered via the same or via a different mode of administration. For example, a huperzine compound with a pharmaceutically acceptable salt or hydrate can be administered orally or can be administered via a transdermal patch, an aerolized formulation, by nasal inhalation, or via nano- or micro-encapsulated formulations. The huperzine compounds can be administered by intrathecal and intraventricular modes of administration.

Various combinations of the huperzine compounds can be administered, e.g., huperzine A and analogs thereof, huperzine B and analogs thereof, or a combination of huperzine A and huperzine B or their various analogs. Huperzine analogs are known in the art, e.g., ZT-1 (Debiopharm, Switzerland); RE38,460, Ma et al., 2004, Nat. Prod. Rep. 21:752-772; Zhou et al., 2004, Neuroscience Letters 313:137-140. In addition, the compounds can be administered in a combination with other therapeutic agents. Of course, the choice of therapeutic agents that can be co-administered with the composition of the invention will depend, in part, on the condition being treated. For example, the compounds of the invention can be administered in cocktails comprising other agents used to treat the pain and other symptoms and side effects commonly associated with epilepsy or seizures.

The huperzine compounds can be formulated either as single compounds per se or as mixtures of compounds of the same type (e.g., two different analogs), as well as mixtures of huperzine compounds (e.g. huperzine A and huperzine B). Such compositions will generally comprise a huperzine compound formulated as a pharmaceutically acceptable salt or hydrate.

Pharmaceutical compositions for use in accordance with the present invention can be formulated in conventional manner using one or more physiologically acceptable carriers, excipients, diluents or auxiliaries that further facilitate processing of the huperzine compounds. The choice of formulation is dependent upon the selected administration route.

The formulations can be administered by implantation or transcutaneous delivery (for example subcutaneously or intramuscularly), intramuscular injection, or transdermally. Thus, for example, the huperzine compounds can be formulated with suitable polymeric or hydrophobic materials (such as an emulsion in an acceptable oil) or ion exchange resins.

Formulations suitable for transdermal administration of compounds are described in U.S. Pat. Nos. 5,725,876; 5,716,635; 5,633,008; 5,603,947; 5,411,739; 5,364,630; 5,230,896; 5,004,610; 4,943,435; 4,908,213; and 4,839,174, which patents are hereby incorporated herein by reference. As huperzine compounds, pharmaceutically acceptable salts or hydrates are readily absorbed and cross cell membranes and the blood-brain barrier. Any of these formulations can be routinely adapted for transdermal administration.

For injection, the huperzine compounds can be formulated in physiologically compatible aqueous solutions, such as Hanks's solution, Ringer's solution, or physiological saline buffer. For transmucosal administration, penetrants appropriate to the barrier to be permeated are used in the formulation. Such penetrants are generally known in the art.

For oral administration, the huperzine compounds can be formulated with pharmaceutically acceptable carriers well known in the art. Such carriers enable the compounds of the invention to be formulated for oral administration as tablets, pills, gums dragees, capsules, liquids, gels, syrups, slurries, suspensions and the like. Alternatively, the compounds can be formulated into candies, cookies, or other edible foodstuffs. Pharmaceutical preparations for oral use can be obtained by mixing the compounds of the invention with a solid excipient, optionally grinding the resulting mixture, and processing the mixture of granules, after adding suitable auxiliaries, if desired, to obtain tablets or dragee cores. Suitable excipients include, but are not limited to, fillers, such as sugars, including lactose, sucrose, mannitol, or sorbitol; cellulose preparations, such as maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as cross-linked polyvinyl pyrrolidone, agar, or alginic acid or a salt thereof, such as sodium alginate.

Concentrated sugar solutions can be used that can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the compounds of the invention in an admixture with filler, such as lactose; binders, such as starches; or lubricants, such as talc or magnesium stearate; or stabilizers. In soft capsules, the compounds of the invention can be dissolved or suspended in suitable liquids, such as fatty oils, liquid paraffin, or liquid polyethylene glycols. In addition, stabilizers can be added to the soft-capsule formulation. All formulations for oral administration should be in dosages suitable for such administration.

For buccal administration, the compositions can take the form of oral sprays, tablets, gums, or lozenges formulated by well-known methods. A candy formulation suitable for oral or buccal administration of therapeutic compounds, pharmaceutically acceptable salts and hydrates is described in U.S. Pat. No. 6,083,962, which is hereby incorporated herein by reference. Additional formulations suitable for oral or buccal administration of therapeutic compounds, are described in U.S. Pat. Nos. 5,939,100; 5,799,633; 5,662,920; 5,603,947; 5,549,906; D358,683; 5,326,563; 5,293,883; 5,147,654; 5,035,252; 4,967,773; 4,907,606; 4,848,376; and 4,776,353, which are hereby incorporated herein by reference. All of these formulations can be routinely adapted for administration of huperzine compounds, pharmaceutically acceptable salts and hydrates.

Compositions for inhalation or insufflation include solutions and suspensions in pharmaceutically acceptable, aqueous or organic solvents, or mixtures thereof, and powders. Preferably the compositions are administered by the oral or nasal respiratory route for local or systemic effect. For administration by oral or nasal inhalation, the compounds of the invention are conveniently delivered in the form of an aerosol spray delivered via pressurized packs or a nebulizer, with a suitable propellant, e.g., carbon dioxide or other suitable gas. In the case of a pressurized aerosol, the dosage unit can be controlled by a dose-metered valve. Capsules and cartridges, e.g. gelatin, for use in an inhaler or insufflator can be formulated as a powder mix of the compounds if the invention and a suitable powder base, such as lactose or starch. Formulations suitable for nasal inhalation are well known in the art. For example, a nasal aerosol spray may contain huperzine, a water soluble diluent such as an organic acid, and a thickening agent such as a natural or synthetic polymer or an oil substance comprising the oil phase of an emulsion. The compounds of the invention can also be administered in a vaporizer that delivers a volume of vapor containing huperzine. The vaporizer can be battery operated and designed to deliver a dosage of huperzine effective to inhibit seizures. The compounds of the invention, in a sterile pharmaceutically acceptable solvent, may be nebulized by use of inert gases. Nebulized solutions may be breathed directly from the nebulizing device or the nebulizing device may be attached to a face mask, tent or intermittent positive pressure breathing machine.

An aerosol spray containing huperzine is used to treat or prevent seizure clustering. Some patients with epilepsy are prone to having consecutive seizures after the initial seizure. An aerosol formulation of huperzine can be used as a spray mist in such patients after the first seizure as a preventative measure against subsequent seizures. The aerosol formulation is administered in a spray mist in a subject that has been chemically induced to have seizures or is at the risk of developing seizures, such as those at risk of bioterror attacks. In such instances, the aerosolized huperzine can be provided in the form of a portable kit or package and used prior to, or immediately after, exposure to the seizure inducing chemical, e.g., organophosphate.

For administration by injection, the compounds of the invention can be formulated with a surface-active agent (or wetting agent or surfactant) or in the form of an emulsion (as a water-in-oil or oil-in-water, emulsion). Suitable surface-active agents include, but are not limited to, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent may comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil. corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

An injectable formulation containing huperzine can be used to treat or prevent seizure clustering. Some patients with epilepsy are prone to having consecutive seizures after the initial seizure. The injectable formulation of huperzine can be after the first seizure as a preventative measure against subsequent seizures. In another embodiment, the injectable formulation can be administered to a subject that has been chemically induced to have seizures or is at the risk of developing seizures, such as those at risk of bioterror attacks. In such instances, the injectable formulation of huperzine can be provided in the form of a portable kit or package and used prior to, or immediately after, exposure to the seizure inducing chemical, e.g., organophosphate.

The huperzine compounds can be formulated for parenteral administration by injection, e.g., by bolus injection or continuous infusion. Formulations for injection can be presented in unit-dosage form, e.g., in ampules or in multi-dose containers, optionally with an added preservative. The compositions can take such forms as suspensions, solutions, or emulsions in oily or aqueous vehicles, and can contain formulatory agents, such as suspending, stabilizing, or dispersing agents.

Pharmaceutical formulations for parenteral administration include aqueous solutions of the compounds of the invention in water-soluble form. Additionally, suspensions of the compounds of the invention can be prepared as appropriate oily-injection suspensions. Suitable lipophilic solvents or vehicles include fatty oils, such as sesame oil, or synthetic-fatty-acid esters, such as ethyl oleate or triglycerides, or liposomes. Aqueous-injection suspensions can contain substances that increase the viscosity of the suspension, such as sodium carboxymethyl cellulose, sorbitol, or dextran. Optionally, the suspension can contain suitable stabilizers or agents that increase the solubility of the compounds of the invention to allow for the preparation of highly concentrated solutions.

Alternatively, the huperzine compounds can be in powder form for constitution with a suitable vehicle, e.g., sterile pyrogen-free water, before use.

The huperzine compounds can also be formulated in rectal compositions, such as suppositories or retention enemas, e.g., containing conventional suppository bases, such as cocoa butter or other glycerides.

The pharmaceutical compositions also can comprise suitable solid- or gel-phase carriers or excipients. Examples of such carriers or excipients include, but are not limited to, calcium carbonate, calcium phosphate, various sugars, starches, cellulose derivatives, gelatin, and polymers, such as polyethylene glycols.

The appropriate dose of the pharmaceutical composition is that amount effective to prevent occurrence of the symptoms of the disorder or to treat some symptoms of the disorder from which the patient suffers. By “effective amount”, “therapeutic amount” or “effective dose” is meant that amount sufficient to elicit the desired pharmacological or therapeutic effects, thus resulting in effective prevention, treatment, or reduction of symptoms or pain associated with a given disorder. The effective dose can vary, depending upon factors such as the condition of the patient, the severity of the symptoms of the disorder, and the manner in which the pharmaceutical composition is administered. The effective dose of the composition can differ from patient to patient but in general includes amounts starting where desired therapeutic effects occur, but below that amount where significant undesirable side effects are observed. Thus, when treating a seizures and epilepsy, an effective amount of composition is an amount sufficient to pass across the blood-brain barrier of the subject and to interact with relevant receptor sites in the brain of the subject and alter the actions of neurotransmitters on those receptors, thus resulting in effective prevention or treatment of the disorder.

The duration of action, and the therapeutic effect of huperzine may be increased by combining huperzine A and huperzine B without causing adverse side effects. Furthermore, the dosage of huperzine A in combination with huperzine B may be reduced to achieve the same therapeutic effect. For the sake of illustration only, if a dosage of 2000 µg/day of huperzine A is effective at treating seizures, but causes some undesired side effects, then the dosage of huperzine A may be reduced, for example to 1000 µg/day, when used in combination with huperzine B for example, at a dosage of about 30 mg/day. This combination provides the same therapeutic effect but without the adverse side effects. Furthermore, the duration of therapeutic effect may also increase by a using a combination of huperzine A and huperzine B. As will be obvious to the skilled practitioner, the effective dosage amount can be manipulated to achieve the desired therapeutic effect.

Depending upon the neuroprotective effect desired, the huperzine compounds can be administered to achieve either a therapeutic or a prophylactic effect. For example, the huperzine compounds can be prophylactically administered to a subject who has not yet suffered a seizure, but one who may be prone to, or at risk of seizures, for example as a result of a stroke, thereby protecting the subject against seizures. Alternatively, the huperzine compounds can be administered to subjects who suffer from epilepsy. Regardless of the condition of the subject, the huperzine compounds can typically be administered as part of a daily regimen.

Other disorders that can also be treated include, but are not limited to, cognitive impairment; severe neurodegenerative disorders, such as Alzheimer's disease; and neuronal dysfunction associated with loss of motor skills, such as Parkinson's disease and amyotrophic lateral sclerosis. The compounds of the invention can also treat, prevent, or reverse neuronal dysfunction resulting from CNS injury, such as stroke, spinal-cord injury, and peripheral-nerve injury.

The ratio between toxicity and therapeutic effect for a particular compound is its therapeutic index and can be expressed as the ratio between $TD_{50}$ (the amount of compound causing side effects in 50% of the population) and $ED_{50}$ (the amount of compound effective in 50% of the population). The huperzine compounds that exhibit high therapeutic indices are preferred. Therapeutic index data obtained from animal studies and can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized.

Other embodiments and uses of the invention will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the following claims.

The invention claimed is:

1. A method for reducing the frequency, reducing the severity, or reducing the duration of a seizure comprising identifying a subject who has suffered an acute brain insult, traumatic brain injury, stroke, a central nervous system infection or a central nervous system injury, and fifth; and administering to the subject a composition comprising a purified huperzine compound.

2. The method of claim 1, wherein said subject has suffered a traumatic brain injury.

3. The method of claim 1, wherein said huperzine compound is administered before or at the onset of a seizure.

4. The method of claim 1, wherein said huperzine compound is administered after the occurrence of a seizure.

5. The method of claim 1, said seizure disorder comprises epilepsy.

6. The method of claim 1, wherein said subject is diagnosed with both epilepsy and has a score of less than 27 on a MMSE.

7. The method of claim 1, wherein said purified huperzine comprises at least 99% Huperzine A by weight.

8. The method of claim 1, wherein said huperzine is administered at a dose of 0.1 mg/kg/day to 20 mg/kg/day.

9. The method of claim 1, wherein said subject is administered a dose of less than 0.83 mg/kg/day.

10. The method of claim 1, wherein said subject is administered a dose of between 0.1 and 0.5 mg/kg/day.

11. The method of claim 1, wherein said subject is administered a dose of 0.2 and 0.3 mg/kg/day.

12. The method of claim 1, wherein said subject is administered a dose of 5 mg/kg/day.

13. The method of claim 1, wherein said subject is administered a dose of 10 mg/kg/day.

14. The method of claim 1, wherein said subject is administered a dose of 15 mg/kg/day.

15. The method of claim 1, wherein said subject is administered a dose of 20 mg/kg/day.

16. The method of claim 1, wherein said subject is administered a dose of 30 mg/kg/day.

17. The method of claim 1, wherein the huperzine compound is selected from the group consisting of huperzine A and an analog thereof.

18. The method of claim 1, wherein the huperzine compound is selected from the group consisting of huperzine B and an analog thereof.

19. The method of claim 1, wherein the huperzine compound comprises both huperzine A and huperzine B.

20. The method of claim 1, wherein said huperzine compound comprises ZT-1.

21. The method of claim of claim 1, wherein said huperzine compound is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

22. The method of claim 1, wherein said huperzine compound is administered orally.

23. The method of claim 1, wherein said huperzine compound is administered in the form of a tablet, pill, gum dragee, capsule, liquid, gel, syrup, slurry, or suspension.

24. The method of claim, wherein said huperzine compound is in a sustained release delivery vehicle.

25. The method of claim 24, wherein said vehicle comprises an adhesive dermal patch.

26. The method of claim 24, wherein said vehicle comprises an intravenous pump.

27. The method of claim 24, wherein said vehicle comprises an implant, said implant being biodegradable or erodible.

28. The method of claim 24, wherein said vehicle comprises a semipermeable membrane, said membrane being delivery rate controlling.

29. The method of claim 24, wherein said vehicle comprises a plurality particles, each of said particles comprising a different rate of dissolution.

30. The method of claim 1, wherein said huperzine compound is in the form of an edible foodstuff.

31. The method of claim 30, wherein said foodstuff comprises candies or cookies.

* * * * *

UNITED STATES PATENT AND TRADEMARK OFFICE
CERTIFICATE OF CORRECTION

| | | |
|---|---|---|
| PATENT NO. | : 8,822,492 B2 | Page 1 of 1 |
| APPLICATION NO. | : 13/347136 | |
| DATED | : September 2, 2014 | |
| INVENTOR(S) | : Steven C. Schachter | |

It is certified that error appears in the above-identified patent and that said Letters Patent is hereby corrected as shown below:

In the Claims

Column 34, claim 1, line 1, after "injury," delete the words "and fifth;"

Signed and Sealed this
Thirtieth Day of December, 2014

Michelle K. Lee
*Deputy Director of the United States Patent and Trademark Office*